US012806427B2

(12) United States Patent
Bauer et al.

(10) Patent No.: US 12,806,427 B2
(45) Date of Patent: Nov. 24, 2026

(54) LEADLESS CARDIAC CONDUCTION SYSTEM PACING PACEMAKER AND THE DELIVERY SYSTEM

(71) Applicant: Singular Medical (USA) Inc., Irvine, CA (US)

(72) Inventors: Ryan Bauer, Irvine, CA (US); Martin Tze, Irvine, CA (US); Scott Hayden, Irvine, CA (US); Yongxing Zhang, Irvine, CA (US); Matthew Stenzel, Irvine, CA (US); Lichuan Ping, Irvine, CA (US); Entao Liu, Irvine, CA (US)

(73) Assignee: Singular Medical (USA) Inc., Irvine, CA (US)

( * ) Notice: Subject to any disclaimer, the term of this patent is extended or adjusted under 35 U.S.C. 154(b) by 1021 days.

(21) Appl. No.: 17/811,151

(22) Filed: Jul. 7, 2022

(65) Prior Publication Data

US 2024/0009468 A1 Jan. 11, 2024

(51) Int. Cl.
*A61N 1/375* (2006.01)
*A61N 1/05* (2006.01)
*A61N 1/362* (2006.01)

(52) U.S. Cl.
CPC ......... *A61N 1/3756* (2013.01); *A61N 1/0573* (2013.01); *A61N 1/37518* (2017.08)

(58) Field of Classification Search
CPC . A61N 1/0573; A61N 1/37518; A61N 1/3756
See application file for complete search history.

(56) References Cited

U.S. PATENT DOCUMENTS

| | | | | |
|---|---|---|---|---|
| 8,634,919 B1 * | 1/2014 | Hou | ........................ | A61N 1/368 607/36 |
| 11,229,798 B2 * | 1/2022 | Toy | ........................ | A61N 1/3756 |
| 2004/0127967 A1 * | 7/2004 | Osypka | .................. | A61N 1/059 607/122 |
| 2009/0082828 A1 * | 3/2009 | Ostroff | ............... | A61N 1/37205 607/9 |
| 2013/0116738 A1 * | 5/2013 | Samade | ............... | A61N 1/3684 607/9 |
| 2015/0025612 A1 * | 1/2015 | Haasl | ................... | A61N 1/0573 607/127 |
| 2018/0050208 A1 * | 2/2018 | Shuros | ............... | A61N 1/36843 |
| 2019/0083800 A1 * | 3/2019 | Yang | .................... | A61N 1/3756 |
| 2019/0351236 A1 * | 11/2019 | Koop | ................... | A61N 1/3756 |
| 2020/0261734 A1 * | 8/2020 | Yang | .................... | A61N 1/0573 |
| 2020/0289835 A1 * | 9/2020 | Eby | ....................... | A61N 1/3756 |
| 2020/0398045 A1 * | 12/2020 | Anderson | .............. | A61N 1/059 |
| 2021/0023367 A1 * | 1/2021 | Ghosh | .................. | A61N 1/0573 |
| 2021/0228887 A1 * | 7/2021 | Doerr | ................... | A61N 1/3708 |
| 2021/0275824 A1 * | 9/2021 | Rock | ...................... | A61N 1/368 |

* cited by examiner

*Primary Examiner* — Brian T Gedeon
(74) *Attorney, Agent, or Firm* — HSML P.C.

(57) ABSTRACT

Leadless pacemakers and methods of implanting the same are provided for a cardiac conduction system. A leadless pacemaker includes an implantable housing including a mounting interface, an electronic circuitry and a power source received by the implantable housing, and an electrode system connected to the electronic circuitry via the mounting interface. The electrode system includes electrodes configured to insert into a septum and having a length to reach pathways of the cardiac conduction system.

20 Claims, 14 Drawing Sheets

LEADLESS CARDIAC CONDUCTION SYSTEM PACING PACEMAKER AND THE DELIVERY SYSTEM

TECHNICAL FIELD

This disclosure relates generally to systems, methods, and designs of leadless pacemakers for the cardiac conduction system. More specifically, the disclosure relates to systems and designs of leadless pacemaker(s) for the cardiac conduction system, and relates to methods of implanting the leadless pacemaker(s).

BACKGROUND

An implantable pulse generator (e.g., an implantable pacemaker, an implantable cardioverter-defibrillator, etc.) is a medical device powered by a battery, contains electronic circuitry having a controller, and delivers and regulates electrical impulses to an organ or a system such as the heart, the nervous system, or the like. A catheter is a tubular medical device for insertion into canals, vessels, passageways, or body cavities usually to keep a passage open to facilitate the delivery of e.g., a leadless device during a surgical procedure. The process of inserting a catheter is "catheterization". The conduction system of the heart consists of cardiac muscle cells and conducting fibers that are specialized for initiating impulses and conducting the impulses through the heart. The cardiac conduction system initiates the normal cardiac cycle, coordinates the contractions of cardiac chambers, and provides the heart its automatic rhythmic beat. Conduction system pacing (CSP) is a technique of pacing that involves implantation of pacing electrodes along different sites or pathways of the cardiac conduction system and includes His-bundle pacing, left bundle branch pacing, right bundle branch pacing, and/or bilateral pacing (pacing both the left bundle branch and the right bundle branch).

SUMMARY

This disclosure relates generally to systems, methods, and designs of leadless pacemakers for the cardiac conduction system. More specifically, the disclosure relates to systems and designs of leadless pacemakers including electrodes to insert into a septum of cardiac conduction system, and relates to methods of making and using (implanting) the leadless pacemakers.

Briefly, in one aspect, the present disclosure describes a leadless pacemaker for a cardiac conduction system, including an implantable housing including a mounting interface, an electronic circuitry and a power source received by the implantable housing, and an electrode system connected to the electronic circuitry via the mounting interface. The electrode system includes one or more electrodes configured to insert into a septum and having a length to reach one or more of a His-bundle, a right bundle branch (RBB), and a left bundle branch (LBB).

In another aspect, the present disclosure describes a wireless pacemaker for a cardiac conduction system, including an implantable housing, an electronic circuitry, and a battery or a wireless power source received by the implantable housing, and an electrode system disposed on an outer surface of the implantable housing and connected to the electronic circuitry inside the implantable housing.

In another aspect, the present disclosure describes a delivery system delivering a leadless pacemaker or a wireless pacemaker described herein. The system further includes a torque shaft, and a delivery catheter including a flexible, deflectable catheter shaft to receive the torque shaft, and a catheter housing connecting to the flexible, deflectable catheter shaft at a distal end of the delivery catheter. The catheter housing is configured to receive the pacemaker, and the torque shaft extends in the flexible, deflectable catheter shaft and has a distal end rotatablely connected to the pacemaker.

In another aspect, the present disclosure describes a method of implanting a leadless pacemaker for a cardiac conduction system. The method includes positioning the leadless pacemaker inside a catheter, inserting a catheter to reach a septum, positioning the catheter against the septum, inserting the leadless pacemaker through an orifice of the catheter extending from a distal end of the catheter to a proximal end of the catheter, engaging at least one electrode of the leadless pacemaker to the septum, and removing the catheter.

In another aspect, the present disclosure describes a delivery system to deliver a pacemaker described herein. The delivery system includes a guidewire including a wire configured to extend through a through hole of the pacemaker; and a helix tip disposed at a distal end of the wire and configured to be a fixation mechanism and/or a mapping electrode.

In another aspect, the present disclosure describes a method of implanting a leadless pacemaker for a cardiac conduction system. The method includes delivering a guidewire to reach a septum, wherein the guidewire includes a wire and helix tip disposed at a distal end of the wire; fixating the helix tip of the guidewire into the septum; positioning a leadless pacemaker such that the guidewire extends through a through hole of the leadless pacemaker; delivering the leadless pacemaker over the guidewire to reach the septum; engaging at least one electrode of the leadless pacemaker to the septum; and removing the guidewire from the septum.

Various advantages are obtained in exemplary embodiments of the disclosure. One such advantage is that embodiments disclosed herein can provide a leadless device having its electrode system seated into the septum (e.g., inserted inside the septum in an adequate distance, e.g., one or more electrodes being inserted into the tissue of the septum) of the cardiac conduction system (e.g., to reach the pathway such as the LBB from the cavity of the right ventricle). Some embodiments of devices, systems, and methods described herein provides a leadless pacemaker which refers to a self-contained device that is inserted to the heart. In some cases, a leadless pacemaker includes a self-contained pulse generator and electrode system implanted directly into the right ventricle, omitting the need for a generator pocket and transvenous lead(s) as required by a typical transvenous pacemaker. In some embodiments of devices, systems, and methods described herein, an electrode system is directly connected, via a mounting interface, to an implantable housing receiving the pulse generator and electronic circuitries, such that the device as whole can be implanted inside the organ or system (e.g., a heart). In addition, the electrode system of a leadless pacemaker described herein include one or more electrodes configured to insert into a septum and having a length to reach cardiac conduction pathways including a His-bundle, a right bundle branch (RBB), and a left bundle branch (LBB) when the leadless device is implanted inside the organ or system (e.g., a heart).

Embodiments disclosed herein can also provide a catheter that can be more atraumatic and easier to be delivered to a desired location. Embodiments disclosed herein can further provide a catheter that can minimize the trauma to the heart tissue and facilitate ease of leadless lead implantation and consequently result in stable electrical performance of the pacing system.

Various aspects and advantages of exemplary embodiments of the disclosure have been summarized. The above Summary is not intended to describe each illustrated embodiment. Other features and aspects will become apparent by consideration of the following detailed description and accompanying drawings.

BRIEF DESCRIPTION OF THE DRAWINGS

References are made to the accompanying drawings that form a part of this disclosure and which illustrate the embodiments in which systems and methods described in this specification can be practiced.

Figure 1A:
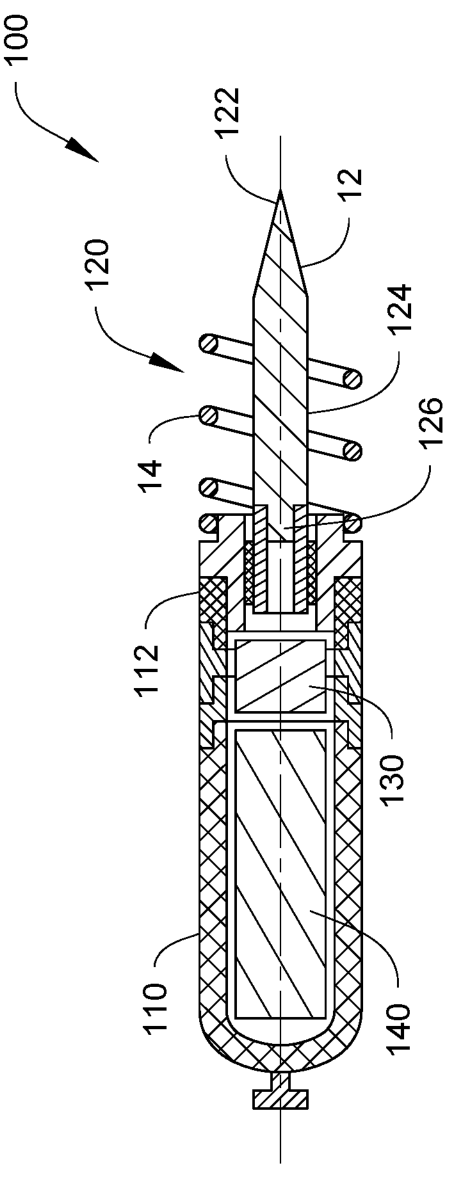
FIG. 1A is a cross-sectional view of a leadless device, according to an embodiment.

Particular embodiments of the present disclosure are described herein with reference to the accompanying drawings; however, it is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. In this description, as well as in the drawings, like-referenced numbers represent like elements that may perform the same, similar, or equivalent functions.

DETAILED DESCRIPTION

This disclosure relates generally to systems, methods, and designs of catheter and leadless devices for a cardiac conduction system. More specifically, the disclosure relates to systems and designs of catheter and leadless device(s) including an electrode system for the cardiac conduction system, and relates to methods of implanting the leadless device(s) for the cardiac conduction system using a catheter system including the catheter.

As defined herein, the phrase "distal" may refer to being situated away from a point of attachment (e.g., to a device such as the implantable pulse generator) or from an operator (e.g., a physician, a user, etc.). A distal end of a device or a catheter may refer to an end of the device or the catheter that is away from the operator or from a point of attachment to the implantable pulse generator.

As defined herein, the phrase "proximal" may refer to being situated nearer to a point of attachment (e.g., to a device such as the implantable pulse generator) or to an operator (e.g., a physician, a user, etc.). A proximal end of a device or a catheter may refer to an end of the device or the catheter that is close to the operator or to a point of attachment to the implantable pulse generator.

As defined herein, the phrase "French" may refer to a unit to measure the size (e.g., diameter or the like) of device such as a catheter, a sheath, an electrode, a rod, a capsule casing, etc. For example, a round catheter or device of one (1) French has an external diameter of ⅓ millimeters. For example, if the French size is 9, the diameter is 9/3=3.0 millimeters.

As defined herein, the phrase "helix" may refer to (e.g., an object) having a three-dimensional shape like that of a wire wound (e.g., in a single layer) around a cylinder or cone, as in a corkscrew or spiral staircase. The phrase "linear" may refer to being arranged in or extending straightly or nearly straightly.

As defined herein, the phrase "conductive" may refer to electrically conductive.

As defined herein, the phrase "septum" may refer to a partition separating two chambers, such as that between the chambers of the heart. Septum can be atrial septum and/or ventricular septum. The phrase "ventricular septum" or "inter-ventricular septum" may refer to a partition separating two ventricular chambers. The phrase "right ventricular septum" may refer to the ventricular septum where the RBB is located, while "left ventricular septum" may refer to the ventricular septum where the LBB is located.

As defined herein, the phrase "pacing" may refer to depolarization of the atria or ventricles, resulting from an impulse delivered (e.g., at desired voltage(s) for a desired duration, or the like) from a device (such as a pulse generator) via an electrode system to the heart via myocardium or directly via the cardiac conduction system. The phrase "sensing" may refer to detection by the device of intrinsic atrial or ventricular or conduction system electrical signals that are conducted up an electrode system. It will be appreciated that each of the electrodes described herein can be configured as a pacing electrode and/or a sensing electrode. It will also be appreciated that each of the electrodes described herein can be configured as anode and/or cathode. Exemplary methods of using pacing and sensing electrodes were described in U.S. patent application Ser. No. 17/804,767, which is incorporated by reference herein.

As defined herein, the phrase "conduction system pacing" or "CSP" may refer to a therapy that involves the placement of pacing electrode system along different sites or pathways of the cardiac conduction system with the intent of overcoming sites of atrioventricular conduction disease and delay, thereby providing a pacing solution that results in more synchronized biventricular activation. Electrode placement for CSP can be targeted at the bundle of His, known as His-bundle pacing (HBP), at the region of the left bundle branch (LBB), known as LBB pacing (LBBP), or at the region of the right bundle branch (RBB), known as RBB pacing (RBBP) or both at the regions of RBB and LBB for Bi-lateral Bundle Branch Pacing (BBBP). Compared with conventional right ventricular (RV) pacing or biventricular (RV and left ventricular (LV)) pacing, where RV apical pacing electrode system and/or LV epicardial electrode system are implanted, the electrode system for CSP is placed through the septum e.g., closer to the His-bundle, the LBB, and/or the RBB. As such, the design, function, and purpose of leadless devices described herein for cardiac conduction system are different from those of the lead(s) for RV and/or LV pacing. It will be appreciated that ventricular pacing (e.g., RV pacing or the like) may be un-physiological and may result in adverse outcomes of mitral and/or tricuspid regurgitations, atrial fibrillation, heart failure, and/or pacing induced cardiomyopathy. CSP can be physiological pacing that can results in electrical-mechanical synchronization to mitigate chronic clinical detrimental consequence including e.g., pacing induced cardiomyopathy. It will also be appreciated that CSP indications may include e.g., a high burden of ventricular pacing being necessary (e.g., permanent atrial fibrillation with atrioventricular block, slowly conducted atrial fibrillation, pacing induced cardiomyopathy, atrioventricular node ablation, etc.); sick sinus syndrome, when atrioventricular node conduction diseases exist; and/or an alternative to biventricular pacing in heart failure patients with bundle branch block, narrow QRS and PR prolongation, biventricular pacing no-responders or patients need biventricular pacing cardiac resynchronization therapy upgrade, or the like.

Some embodiments of the present application are described in detail with reference to the accompanying drawings so that the advantages and features of the present application can be more readily understood by those skilled in the art. The terms "near", "far", "top", "bottom", "left", "right", and the like described in the present application are defined according to the typical observation angle of a person skilled in the art and for the convenience of the description. These terms are not limited to specific directions.

Processes described herein may include one or more operations, actions, or functions depicted by one or more blocks. It will also be appreciated that although illustrated as discrete blocks, the operations, actions, or functions described as being in various blocks may be divided into additional blocks, combined into fewer blocks, or eliminated, depending on the desired implementation. Any features described in one embodiment may be combined with or incorporated/used into the other embodiment, and vice versa. The scope of the disclosure should be determined by the appended claims and their legal equivalents, rather than by the examples given herein. For example, the steps recited in any method claims may be executed in any order and are not limited to the order presented in the claims. Moreover, no element is essential to the practice of the disclosure unless specifically described herein as "critical" or "essential."

FIG. 1A is a cross-sectional view of a leadless device 100, according to an embodiment. The leadless device 100 includes an implantable housing 110 including a mounting interface 112 connecting to an electrode system 120. The implantable housing 110 receives an electronic circuitry 130 and a power source 140. The housing 110 can be made of any suitable material such as, for example, ceramics, titanium, plastic, etc., to protect the components received by the housing 110. The housing 110 may have a substantially cylindrical capsule structure with an outer diameter in the range, for example, from at or around 1 mm to at or around 4 mm, from at or around 4 mm to at or around 10 mm, or from at or around 4 mm to at or around 8 mm. It is to be understood that the housing 110 may have any suitable shapes such as a solid cylindrical capsule, a tubular structure with a central hole along its axis, etc. As further shown in FIG. 1B, the housing 110 includes a cap 114 with an opening 116 to be enclosed by the mounting interface 112 with the power source 140 and/or the electronic circuitry 130 being received in the cavity 115 thereof. A rotation mechanism (e.g., a drive screw) 113 is provided on the cap 114 to be connected to a torque shaft to facilitate the rotation and screwing of the device into a septum, which will be discussed further below. In some cases, the power source 140 may include one or more batteries. The electronic circuitry 130 may include a pulse generator powered by the power source 140 and a controller to control the pulse generator to deliver and regulate electrical impulses to the electrode system 120 and/or determine sensing signals from the electrode system 120.

A controller described herein refers to a local controller of a pulse generator, both being received by an implantable housing. The local controller may communicate with a remote controller of a specially programmed computer e.g., used by a physician, or any suitable controller(s)). The local controller can include a processor, memory, and/or communication ports to communicate with e.g., other components of the pulse generator or specially programmed computer, and/or communicate with equipment or systems used before, during, and after implanting the pulse generator. The local controller can communicate with other components using any suitable communications including wired and/or wireless, analog and/or digital communications. In an embodiment, the communication can include communications over telematics of the pulse generator or the specially programmed computer, which may be communicatively connected to telematics equipment, mobile device, communication system, cloud, or the like. The pulse generator or the specially programmed computer can include sensors (e.g., sound, acceleration, temperature, pressure, motion, voltage, current, battery status, battery charging level, or the like), or the pulse generator or the specially programmed computer can communicate with such sensors. The controller can obtain data sensed by the sensors and control the settings of the sensors and/or the components of the pulse generator or the specially programmed computer.

An electrode system described herein may include one or more electrodes configured to insert into a septum and having a length to reach cardiac conduction pathways including a His-bundle, a right bundle branch (RBB), and a left bundle branch (LBB) when the leadless device is implanted inside the organ or system (e.g., a heart). An electrode can act as a pacing electrode to deliver pacing a location in conduction pathways including the His-bundle, the RBB, and/or the LBB. An electrode can also act as a sensing electrode to conduct sensing of electrical signal(s) at the organ (e.g., the hear). A controller (local or remote) can set or configure the electrodes as pacing electrode(s), sensing electrode(s), any combinations of pacing electrode(s) and sensing electrode(s), or being idle. For example, in a unipolar configuration, a first electrode can be set or configured as cathode, and a second electrode can be set or configured as a sensing electrode. In a bipolar configuration, a first electrode can be set or configured as cathode, a second electrode can be set or configured as anode, and a third electrode can be a sensing electrode. It will be appreciated that the configured sensing electrode(s) described herein, which is not involved in pacing, can sense or detect sensing signals, and can provide better accuracy and be more reliable than sensing signals detected from the same pacing electrode that is reused as a sensing electrode. It will also be appreciated that a third electrode described herein can be used for activation determination and to safely and accurately determine the sensing signals.

In the depicted embodiment of FIG. 1A, the electrode system 120 includes a linear electrode 12 having a tapered tip 122 and a rod 124 integral to the tapered tip 122. The rod 124 has its proximate end 126 mounted at the mounting interface 112 and electrically connected to the electronic circuitry 130. It is to be understood that in some cases, a linear electrode may be an auger electrode such as a helix auger where an outer surface of the rod and/or the tip of the linear electrode is threaded for deep seating the linear electrode. It will be appreciated that a linear electrode may have other desired configurations.

The electrode system 120 further includes a helix structure 14 wrapping around the rod 124 of the linear electrode 12. The helix structure has its proximate end mounted at the mounting interface 112 and its distal end extending toward the tapered tip 122 of the linear electrode 12. When acting as electrodes, a linear electrode and a helix structure may include any suitable electrically conductive materials such as, for example, metal or metal alloys (e.g., tantalum, Pt/Ir, NiTi alloy, metal or metal alloys with or without TiN or IrOx coating, etc.). When acting as fixation structures, a linear needle structure and a helix structure may include any non-conductive materials with suitable mechanical properties. The linear electrode may have a length in a range, for example, from at or around 1 mm to at or around 15 mm. The linear electrode may include an active electrode length, for example, from at or around 1 mm to at or around 5 mm, and a non-conductive section with a length, for example, from 0 to at or around 11 mm. The linear electrode may have a diameter, for example, from at or around 0.1 mm to at or around 1 mm. The helix structure may have a wire diameter in a range, for example, from at or around mm to at or around 4 mm. It is to be understood that the mounting interface 112 may include any suitable connecting and mounting components such as, for example, an electrical connector (e.g., one or more of a unipolar feedthrough, a bipolar feedthrough, a weld sleeve joint, a coil, a winding, etc.) and/or an electrically insulating structure (e.g., ceramic) to mount one or more electrodes (e.g., linear electrodes and/or helix electrodes) and fixation structures to the implantable housing 110, and to electrically connect the electrodes to the electronic circuitry 130 received by the housing 110.

In the embodiment depicted in FIG. 1A, the helix structure 14 has an inner diameter greater than the outer diameter of the rod 124 such that the helix structure 14 and the rod 124 may move axially with respect to each other between a "retracted state" and an "extended state". The electrode system 120 is in a "retracted state" when the linear electrode 12 is fully or partially retracted proximally or the helix structure 12 is fully or partially extended distally (e.g., a distal end 122 of the linear electrode is proximal to a distal end of the helix structure 14). The electrode system 120 is in an "extended state" when the linear electrode 12 is fully or partially extended distally or the helix structure 12 is fully or partially retracted proximally (e.g., a distal end 122 of the linear electrode 12 is distal to a distal end of the helix structure 14). FIG. 1A shows the electrode system 120 in an extended state.

In some cases, the linear electrode 12 can be a single polar electrode (e.g., cathode). In some cases, the linear electrode 12 can be a bipolar electrode including e.g., a distal cathode adjacent to the distal end 122, a proximal anode adjacent to the proximal end 126, and a non-conductive middle portion between the distal cathode and the proximal anode. The linear electrode 12 can have a length, for example, at or around 1 mm to at or around 13 mm. The distal cathode of the linear electrode 12 can have a length from at or around 1 mm to at or around 4 mm, the non-conductive middle portion can have a length from at or around 2 mm to at or around 8 mm, and the proximal anode can have a length from at or around 1 mm to at or around 4 mm. It is to be understood that the lengths of an electrode or its parts may vary according to desired applications.

In some cases, the helix structure 14 may act as a fixation mechanism to facilitate fixation of the device onto, for example, a ventricular septum. For example, the helix structure 14 can be screwed into the ventricular septum and facilitate ease of the electrode system 120 being deep seated. It is to be understood that a fixation mechanism/structure described herein may have various forms such as, for example, a helix, a barb, a hook, a wing, a combination thereof, etc. The fixation mechanism/structure may be made of any suitable material such as, for example, NiTi, Stainless Steel, Titanium, Silicone rubber, or any suitable electrode materials described herein. It is to be understood that a helix structure may act as an electrode, a fixation mechanism, or both of electrode and fixation mechanism.

In some cases, the helix structure 14 may be a second electrode in addition to the linear electrode 12. The helix electrode may be a single polar electrode (e.g., anode). The helix electrode may be a bipolar electrode including e.g., a distal cathode, a non-conductive middle portion, and a proximal anode.

Figure 2:
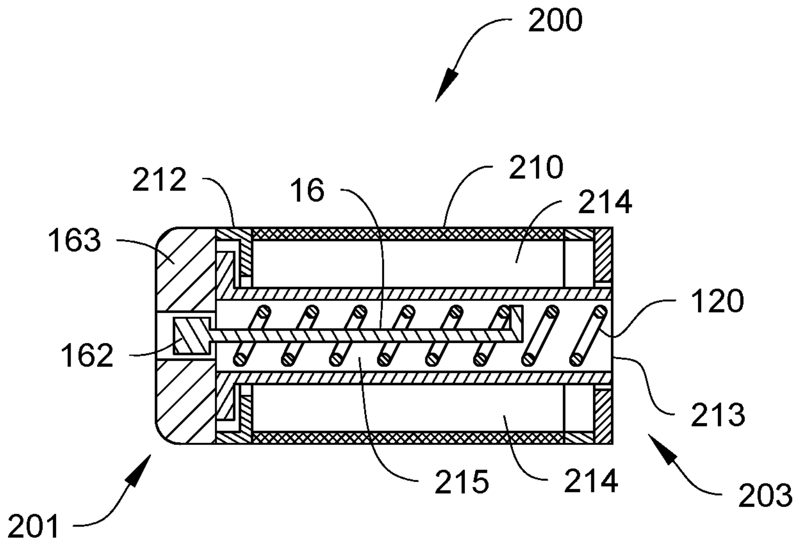
FIG. 2 is a perspective view of a leadless device, according to another embodiment.

FIG. 2 is a cross-sectional view of a leadless device 200, according to another embodiment. The leadless device 200 includes an implantable housing 210 extending between a proximate end 201 and a distal end 203. The implantable housing 210 has a tubular structure including a cavity 215 to receive an electrode system 120 which is connected to a mounting interface 212 at the proximate end 201 of the housing 210. The tubular structure has a hermetic enclosure 214 to receives an electronic circuitry and a power source (not shown). The hermetic enclosure 214 can be made of any suitable material such as, for example, ceramics, titanium, plastic, etc., to protect the components (e.g., batteries, electronic circuitries, etc.) received therein.

The tubular structure has the mounting interface 212 at the proximate end 201 and an opening 213 at the distal end 203. In the depicted embodiment of FIG. 2, the electrode system 120 includes a helix electrode having its proximate end connected to the mounting interface 212 and its distal end located adjacent the opening 213 of the cavity 215. The mounting interface 212 includes a drive mechanism 16 to move the helix electrode between an extended state and a retracted state. When the helix electrode is in the extended state, its length increases and its distal end extends through the opening 213 out of the cavity 215. When the helix electrode is in the retracted state, its length decreases and its distal end retracts through the opening 213 into the cavity 215. In the depicted embodiment of FIG. 2, the drive mechanism includes a drive screw 162 hold by a drive screw retainer 163. The drive mechanism can be connected to a torque shaft to facilitate the rotation and screwing of the device, which will be discussed further below. While a drive screw is used in this embodiment, it is to be understood that any suitable drive mechanism can be used to move a helix electrode or other electrodes between an extended state and a retracted state.

An electrode system described herein may include one or more electrodes in various forms and their combinations. FIGS. 3A-F illustrates various electrode systems of a leadless device, according to some embodiments. In the depicted embodiments, the electrode system 120 is at least partially disposed or placed inside a septum 408, while the housing 110 is disposed or placed inside an adjacent chamber 402 (e.g., the RV chamber). In some cases, the housing 110 is positioned such that the mounting interface 112 is pressed against a side wall 407 of the septum 408. The electrode system 120 is connected to an electronic circuitry (not shown) received by the housing 110 via the mounting interface 112.

Figure 3A:
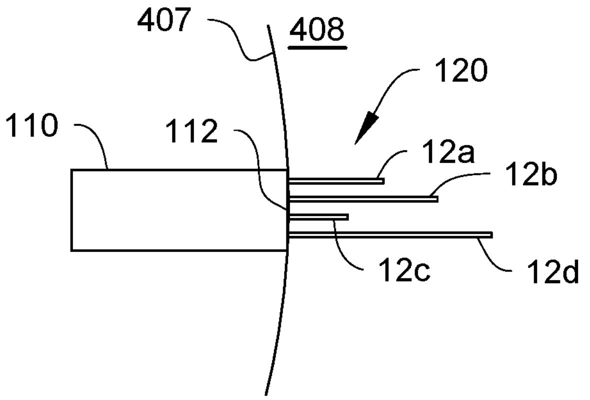
FIG. 3A is a side perspective view of a leadless device, according to an embodiment.

In the embodiment depicted in FIG. 3A, the electrode system 120 includes multiple electrodes 12*a*, 12*b*, 12*c* and 12*d*. The electrodes 12*a*, 12*b*, 12*c* and 12*d* can be linear electrodes or helix electrodes each extending from the mounting interface 112 to a distal end thereof. The electrodes 12*a-d* have different lengths such that the respective distal ends can reach different depths or locations within the septum 408. For example, the electrode 12*a* may have a length such that its distal end is at or around right bundle branch (RBB). The electrode 12*d* may have a greater length such that its distal end is at or around the deeper left bundle branch (LBB). The electrodes may have a length in a range, for example, from at or around 1 mm to at or around 13 mm. In some cases, the longest electrode may have a length in range, for example, from at or around 6 mm to at or around 13 mm. The shortest electrode may have a length in range, for example, from at or around 1 mm to at or around 4 mm. In some cases, the longest electrode may be at least 200% to at least 800% longer than the shortest electrode.

One or more of the electrodes 12*a-d* can be set or configured as a pacing electrode to deliver pacing to a desired location of the septum (e.g., His-bundle pacing, left bundle branch pacing, right bundle branch pacing, and/or bilateral pacing). One or more of the electrodes 12*a-d* can be set or configured as a sensing electrode to conduct sensing of heart electrical signal(s). While four electrodes are illustrated in the embodiment of FIG. 3A, it is to be understood that two or more (e.g., 2, 3, 5, 6-10, etc.) electrodes having different lengths can be used with any combinations of pacing electrodes, sensing electrodes, reference electrodes, or idle electrodes. For example, a first electrode may be located at or around right bundle branch (RBB) and a second electrode may be located at or around left bundle branch (LBB). The varied lengths of the electrodes allow the placing of electrodes at different locations, and allows for the accommodation of different patients' anatomical and/or physiological differences. For example, two electrodes of the electrode system may be located at or around RBB and LBB, respectively, for a first patient, while another two electrodes of the electrode system may be located at or around RBB and LBB, respectively, for a second patient. While linear electrodes are illustrated in the embodiment of FIG. 3A, it is to be understood the electrodes may present in other forms such as, for example, a helix wire.

Figure 3B:
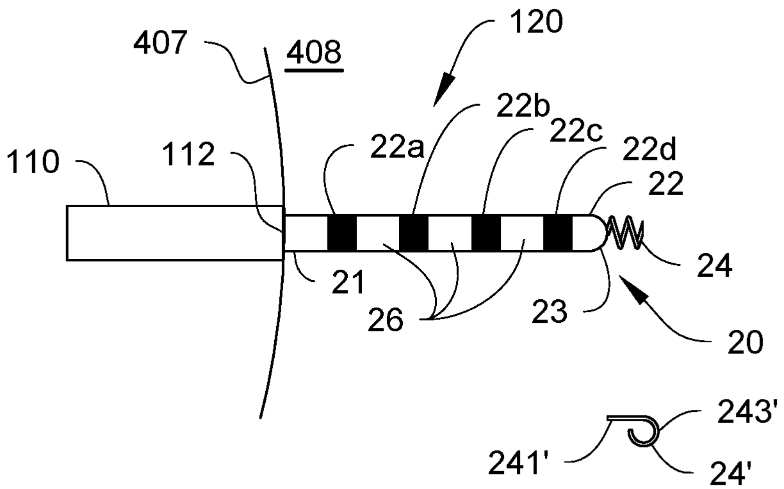
FIG. 3B is a side perspective view of a leadless device, according to another embodiment.

In the embodiment depicted in FIG. 3B, the electrode system 120 includes a rod 20 extending from a proximate end 21 to a distal end 23 thereof. The proximate end 21 is connected to the housing 110 via the mounting interface 112. Multiple electrodes 22*a*, 22*b*, 22*c*, and 22*d* are disposed as an array on the rod 20 between a proximate end 21 and the distal end 23 of the rod 20. In the depicted embodiments, the electrodes 22*a-d* each are a ring electrode disposed around the rod 20 and electrically separated by a spacer 26. The ring electrodes can be made of an electrically conductive material titanium, platinum, platinum-iridium alloy, or the like, and/or coated for increased surface area. The electrodes 22*a-d* are located at different depths of the rod 20 with respect to the proximate end 21, and are electrically connected to the mounting interface 112 via components (not shown) inside the rod 20 (e.g., an electrode coil, an inner electrode, and/or other electrical connectors). Examples of the structure, shape, dimension, and/or material of the helix electrode, the linear electrode, and/or the ring electrode were described in U.S. patent application Ser. No. 17/804,705, which is incorporated by reference herein. Similar to the varied lengths of the electrodes 12*a-d* in the embodiment of FIG. 3A, the varied depths of the electrodes 22*a-d* in the embodiment of FIG. 3B allow the placing of electrodes at different locations of the septum, and allow for the accommodation of different patients' anatomical and/or physiological differences.

The electrode system 120 further includes a fixation structure 24 at the distal end 25 of the rod 20. In the embodiment depicted in FIG. 3B, the fixation structure 24 includes a helix structure which can provide increased fixating force, for example, when the electrode system 120 is screwed into the septum. In addition, such a fixation structure can facilitate active fixation of the electrode system in the septum. In some cases, the fixation structure 24 may include a barb structure 24' having a straight end 241' connected to the distal end of the rod 20 and an angled end 243' to provide passive fixation of the electrode system in the septum. It is to be understood that a fixation structure can be electrically non-conductive. In some cases, a fixation structure may include electrically conductive material(s) and also serve as an electrode (e.g., a pacing electrode, a sensing electrode, or a reference electrode) to electrically connect to an electronic circuitry received by the housing 110.

Figure 3C:
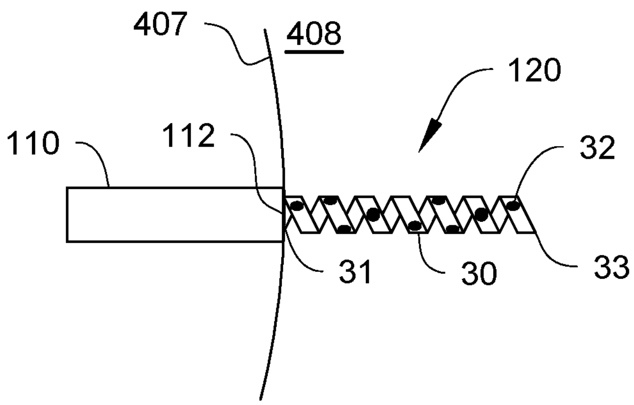
FIG. 3C is a side perspective view of a leadless device, according to another embodiment.
Figure 4A:
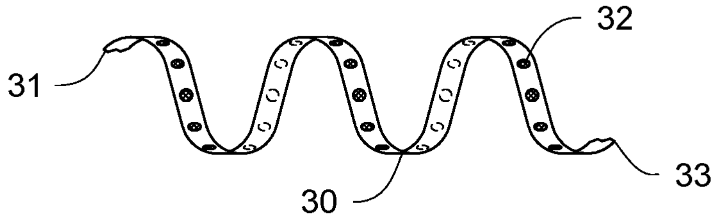
FIG. 4A is a side perspective view of a helix structure, according to an embodiment.

In the embodiment depicted in FIG. 3C, the electrode system 120 includes a helical ribbon structure 30 extending from a proximate end 31 to a distal end 33 thereof. FIG. 4A illustrate a side perspective view of the helical ribbon structure 30. The proximate end 31 is connected to the housing 110 via the mounting interface 112. One or more electrodes 32 are disposed on the helical ribbon structure between the proximate end 31 and the distal end 33. The helical ribbon structure 30 has a rectangular cross-sectional shape with opposite inner and outer surfaces, where the inner surface face to the inner core space defined by the helix. The array of electrodes 32 are arranged on the outer surface with a desired density, e.g., 0.5 to 5 electrodes per revolution. The electrodes 32 can be formed by any suitable methods or processes such as, for example, a surface coating process. In some cases, the helical ribbon structure 30 can include an electrically conductive material the same as or different from that for a helix electrode and/or a linear electrode. An insulating material can be coated on the outer surface of the helical ribbon structure 30 in any desired shapes/patterns to form the array of electrodes 32. In some cases, the helical ribbon structure may have a multi-layer structure using thin-film technology to form multiple electrodes on the respective multiple layers including traces connecting the electrodes to the mounting interface 112. Electrical connectors (not shown) are provided to electrically connect the electrodes 32, via the mounting interface 112, to the electronic circuitry received by the housing 110. Similar to the varied lengths/depths of the electrodes 12*a-d*, 22*a-d* in the embodiment of FIGS. 3A and 3B, the electrodes 32 are located at different depths of the helical ribbon structure 30 with respect to the proximate end 31, which allows the placing of electrodes at different locations of the septum, and allows for the accommodation of different patients' anatomical and/or physiological differences.

While the helical ribbon structure 30 has a rectangular cross-sectional shape, it is to be understood that a helical structure may have any suitable cross-sectional shapes such as, for example, a round shape, an oval shape, etc. In some cases, the electrode system 120 may further include a core disposed in the inner core space of the helical structure 30. The core can be a linear core having one end connected to the mounting interface 112 and the opposite connected to the helical structure 30 to drive the helix structure 30 between an extended state and a retracted state, which may help to insert the device into a heart tissue easier.

Figure 4B:
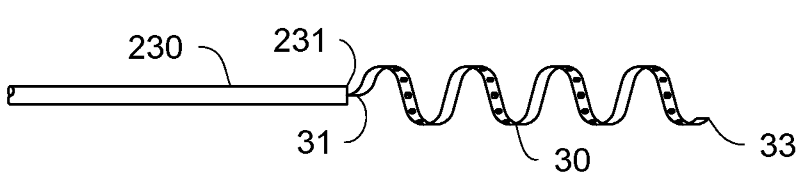
FIG. 4B is a side perspective view of the helix structure of FIG. 4A received by a catheter, according to an embodiment.

A helical or helix structure described herein may be deployed in various ways into a heart tissue (e.g., a septum) as an electrode, a fixation structure, or both. For example, a helix structure can be delivered via a needle structure made of metal. In one embodiment depicted in FIG. 4B, the helical structure 30 is received by a catheter 230. The catheter 230 has an opening 231 from which the helical structure 30 can be extended outside the catheter 230. The catheter 230 has an inner diameter smaller than the outer diameter of helical structure 30 such that when the helical structure 30 is received by the catheter 230, the helical structure 30 is in a straightened state, and when the helical structure 30 extends from the opening 231 of the catheter 230, the helical structure 30 restores its helical profile. The catheter 230 may include an outer layer (e.g., thermoplastic elastomer, or polyurethane), a braid or coil structural element, and an inner layer (e.g., PTFE/HDPE). The catheter 230 may have an inner diameter in the range, for example, from at or around 2 mm to at or around 9 mm. In some cases, the catheter 230 may be flexible and/or deflectable alone or along with the received helical structure 30. In some cases, the helix structure 30 may be bendable at the proximate end 31 such that the extending direction of the helical structure 30 can form an angle with respect to the catheter 230. The angle may be in the range, for example, from at or around 30 degrees to at or around 150 degrees, from at or around degrees to at or around 120 degrees, from at or around 80 degrees to at or around 100 degrees, or at or around 90 degrees.

Figure 1B:
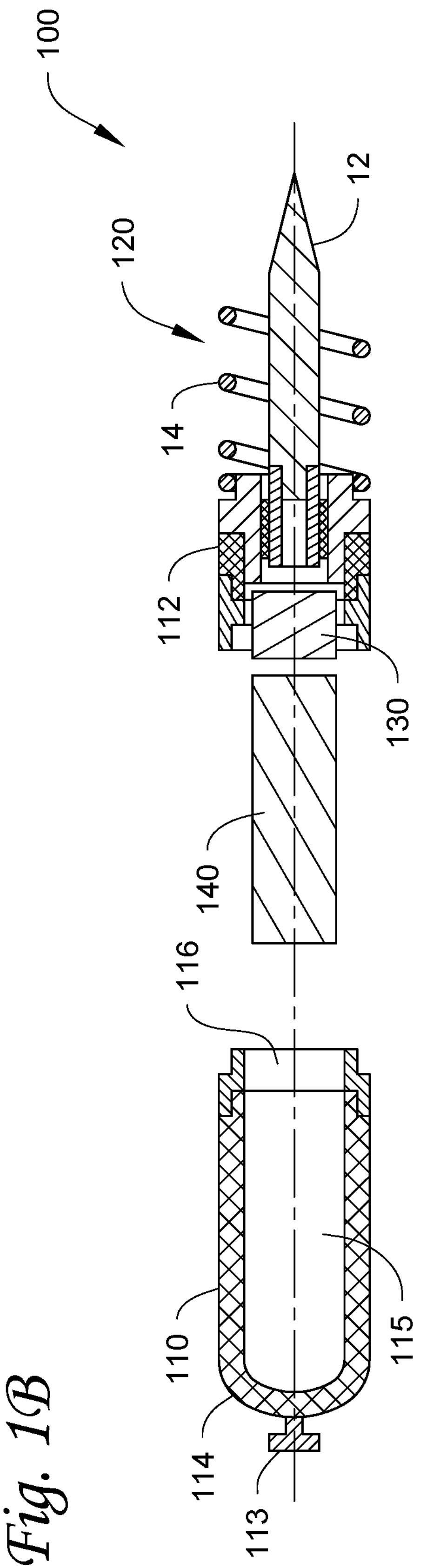
FIG. 1B is an exploded cross-sectional view of the leadless device of FIG. 1A.
Figure 3D:
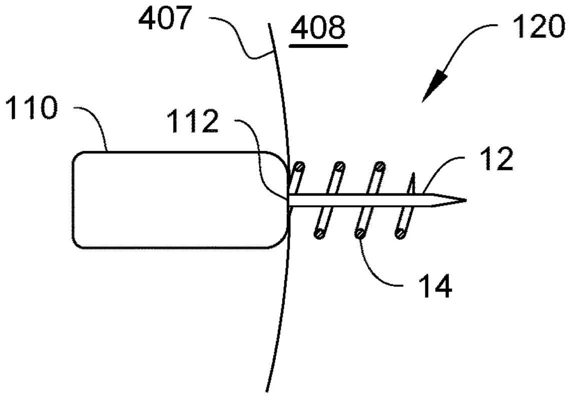
FIG. 3D is a side perspective view of a leadless device, according to an embodiment.

In the embodiment depicted in FIG. 3D, the electrode system 120 includes a linear electrode 12 and a helix electrode 14 connected to the housing 110 via the mounting interface 112. In some cases, the linear electrode 12, the helix electrode 14 and the housing 110 may have a configuration as shown in FIGS. 1A and 1B. The linear electrode 12 has a distal end which is distal to a distal end of the helix electrode 14. In the embodiment depicted in FIG. 3E, the electrode system 120 includes a first helix electrode 14*a* and a second helix electrode 14*b* each connected to the housing 110 via the mounting interface 112. The first and second helix electrodes 14*a*, 14*b* are co-axial. The first helix electrode 14*a* has a distal end which is distal to a distal end of the second helix electrode 14*b*. In the embodiment depicted in FIG. 3F, the electrode system 120 includes a linear electrode 12, a first helix electrode 14*a* and a second helix electrode 14*b* each connected to the housing 110 via the mounting interface 112. The linear electrode 12 has a distal end which is distal to a distal end of the first helix electrode 14*a*. The distal end of the first helix electrode 14*a* is distal to a distal end of the second helix electrode 14*b*.

Figure 3E:
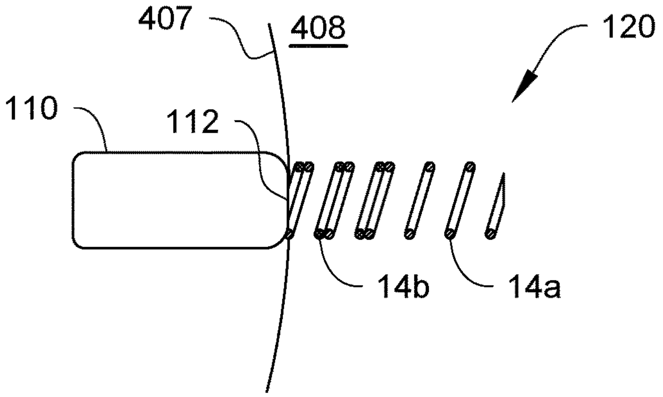
FIG. 3E is a side perspective view of a leadless device, according to another embodiment.
Figure 3F:
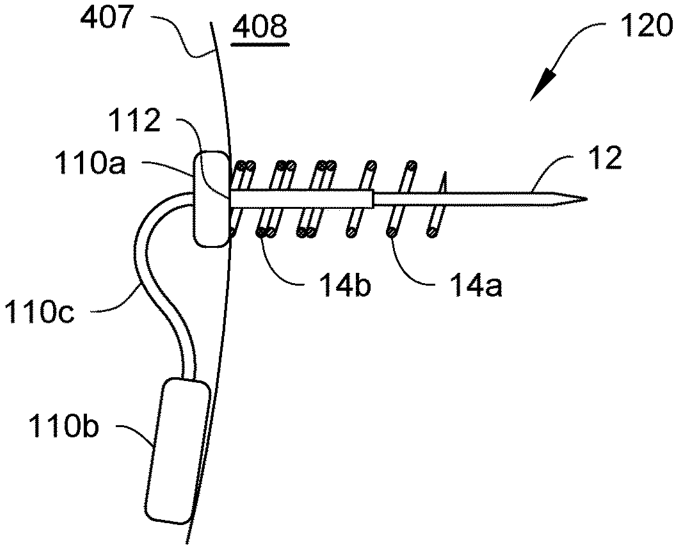
FIG. 3F is a side perspective view of a leadless device, according to another embodiment.

In the embodiments depicted in FIGS. 3E and 3F, the first and second helix electrodes 14*a*, 14*b* are co-radial, i.e., having substantially the same diameters. In some cases, the first and second helix electrodes 14*a*, 14*b* may have different diameters. For example, the second helix electrode may have an outer diameter greater than an outer diameter of the first helix electrode. In some cases, the spacing between windings of a coil of the second helix electrode may be greater than the spacing between windings of a coil of the first helix electrode. The first helix electrode may have a length, for example, at or about four millimeters to or about 12 millimeters. The second helix electrode may have a length, for example, at or about two millimeters to or about six millimeters. It is to be understood that the electrode system 120 may include two or more helix electrodes which can be co-radial, co-axial, or both. Co-radial helix electrodes can be made of small size to facilitate the implant process. Co-axial helix electrodes can facilitate advancing each helix electrode separately (i.e., maneuver of advancing each helix electrode is independent to each other). It is also to be understood that in some cases, at least one of the helix structure may act as a fixation structure, an electrode, or both. It will further be appreciated that the different number of electrodes can provide bipolar, tri-polar, and/or quad-polar sensing and pacing capabilities.

Figure 5A:
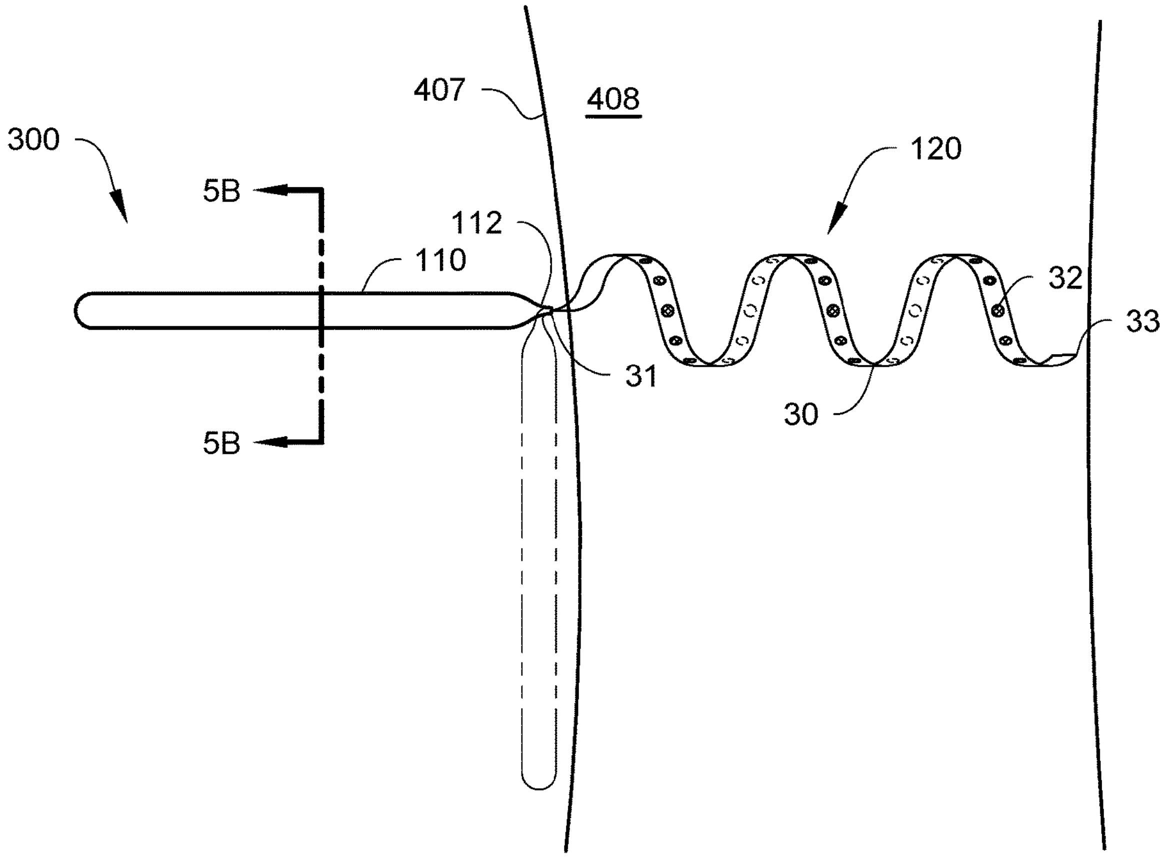
FIG. 5A is a side perspective view of a leadless device, according to an embodiment.
Figure 5B:
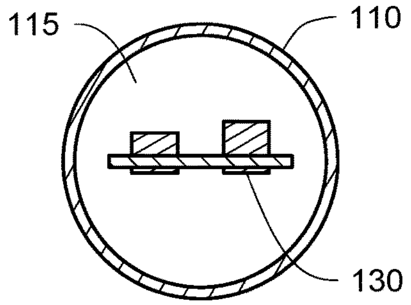
FIG. 5B is a cross-sectional view of the leadless device of FIG. 5A.

In some cases, a leadless device may include a bendable mounting interface such that the implantable housing forms an angle with respect to the electrode system in a range, for example, from at or around 30 degrees to at or around 150 degrees, from at or around 60 degrees to at or around 120 degrees. FIG. 5A illustrates a perspective view of a leadless device 300 including an electrode system 120 disposed in a septum 408. In the depicted embodiment, the electrode system includes the helix structure 30 connected to the implantable housing 110 at the mounting interface 112. The implantable housing 110 has a substantially cylindrical capsule casing defining an enclosed cavity 115 to receive the electronic circuitry 130 as shown in FIG. 5B. The capsule casing may be made of a biocompatible material such as, for example, titanium. The capsule casing may have an outer diameter in the range, for example, from at or around 1 mm to at or around 10 mm, at or around 4 mm to at or around 10 mm, or at or around 4 mm to at or around 8 mm, and a length in the range, for example, from at or around 10 mm to at or around 30 mm. The mounting interface 112 may be bendable such that the extending direction of the helical structure 30 can form an angle with respect to the capsule casing 110 to allow the capsule casing 110 to approach to and/or lay against the side wall 407 of the septum 408. The mounting interface 112 may have a bending angle in the range, for example, from at or around 30 degrees to at or around 150 degrees, from at or around 60 degrees to at or around 120 degrees, from at or around 80 degrees to at or around 100 degrees, or at or around 90 degrees.

In the embodiment depicted in FIGS. 5A-B, the helix structure 30 is a helical ribbon made of an electrically conductive material (e.g., a NiTi alloy). The electrodes 32 can be formed on the ribbon using surface modification technology (SMT) and the array of electrodes 32 can be arranged in any desired shapes/patterns. The ribbon (e.g., NiTi) may extend into the capsule 110 and act as a substrate, where electrically conductive traces and/or SMT components are provided to electrically connect the electrodes 32 to the electronic circuitry 130. While a helix structure is shown in the depicted embodiment of FIG. 5A for the electrode system 120, it is to be understood that the electrode system 120 may include one or more electrodes, one or more fixation structures, and any combinations thereof.

In some cases, an implantable housing described herein may include multiple segmental portions to receive different components such as, e.g., batteries and electronic circuitries. In the embodiment depicted in FIG. 3F, the implantable housing 110 includes a first segmental portion 110*a* and a second segmental portion 110*b* connected to the first segmental portion 110*a* via a flexible segment 110*c*. The first segmental portion 110*a* includes the mounting interface 112 connecting to the electrode system 120, and receives the associated electronic circuitries. The second segmental portion 110*b* receives batteries, and/or the associated electronic circuitries. When the leadless device is disposed inside the heart, the electrode system 120 can be inserted into the septum 408, and the first segmental portion 110*a* is positioned against the side wall 407 of the septum 408. The sheath 110*c* is sufficiently flexible to allow the second segmental portion 110*b* to sag naturally by gravity and lay against the side wall 407 of the septum 408 at a lower position with respect to the first segmental portion 110*a*.

Figure 6:
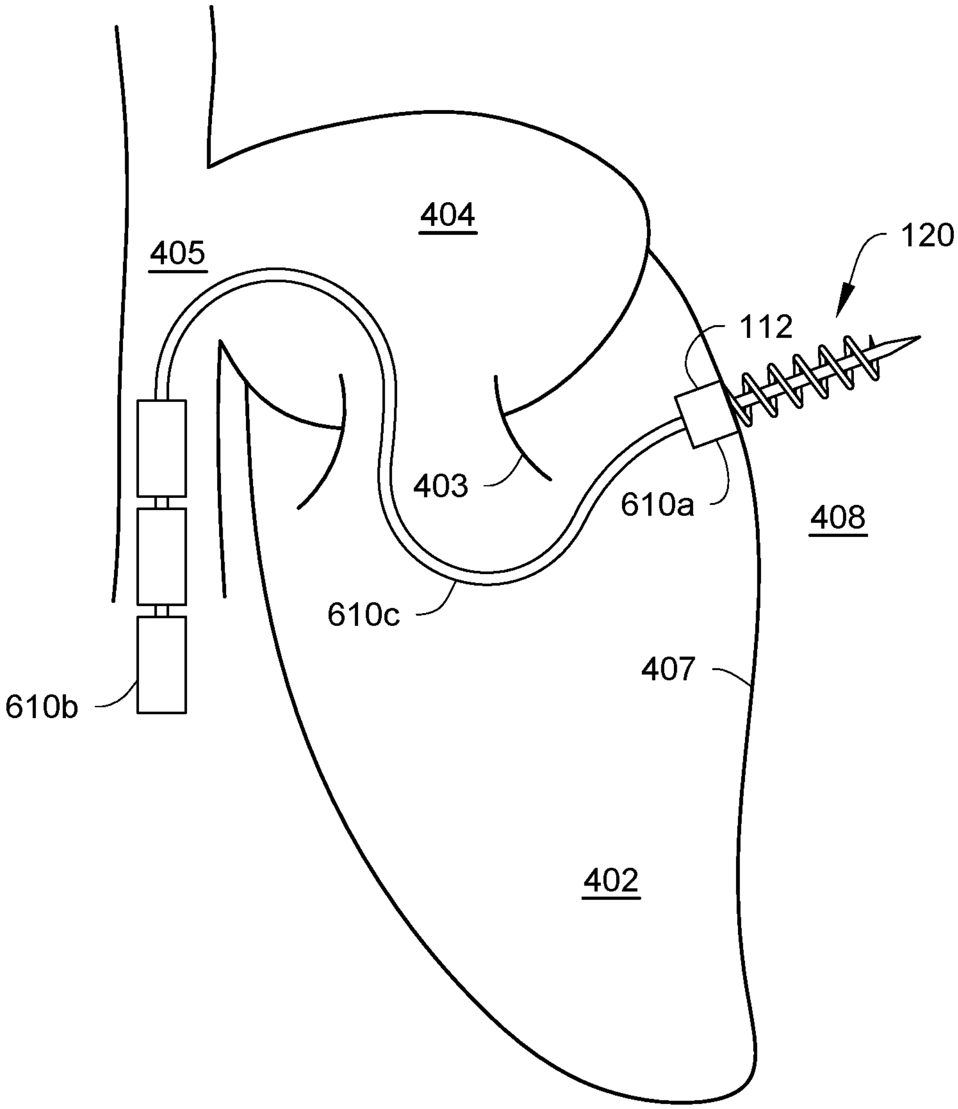
FIG. 6 is a side perspective view of a leadless device implanted in a cardiac conduction system, according to an embodiment.

In the embodiment depicted in FIG. 6, the implantable housing includes a first segmental portion 610*a* and a second segmental portion 610*b* connected to the first segmental portion 610*a* via a flexible segment 610*c*. The first segmental portion 610*a* includes the mounting interface 112 connecting to the electrode system 120, and receives the associated electronic circuitries. The second segmental portion 610*b* may include multiple connected sub-segmental portions to receive multiple batteries, and/or the associated electronic circuitries. When the leadless device is disposed inside the organ (e.g., a heart), the electrode system 120 can be at least partially inserted into the septum 408. While a linear electrode and a helix structure are shown in the depicted embodiment of FIG. 6 for the electrode system 120, it is to be understood that the electrode system 120 may include one or more electrodes, one or more fixation structures, and any combinations thereof. The electrode system 120 is connected to the first segmental portion 610*a* at the mounting interface 112 which is positioned against the side wall 407 of the septum 408. The flexible segment 610*c* connects to the first segmental portion 610*a* at a distal end, extends through the right ventricle (RV) 402, the tricuspid valve 403, and the right atrium (RA) 404, and connects to the second segmental portion 610*b* at a proximate end. The second segmental portion 610*b* sits in the inferior vena cava (IVC) 405. The flexible segment 610*c* has a diameter small enough without interrupting the function of the tricuspid valve 403. The flexible segment 610*c* may include an outer layer (e.g., thermoplastic elastomer, or polyurethane), a braid or coil structural element, and an inner layer (e.g., PTFE/HDPE) to receive conductor materials, and may include one or more other suitable biocompatible materials such as, for example, red rubber, latex, silicone, plastic and/or polyvinyl chloride, or the like. The flexible segment 610*c* may have a diameter, for example, no greater than at or around 4 mm.

Figure 7:
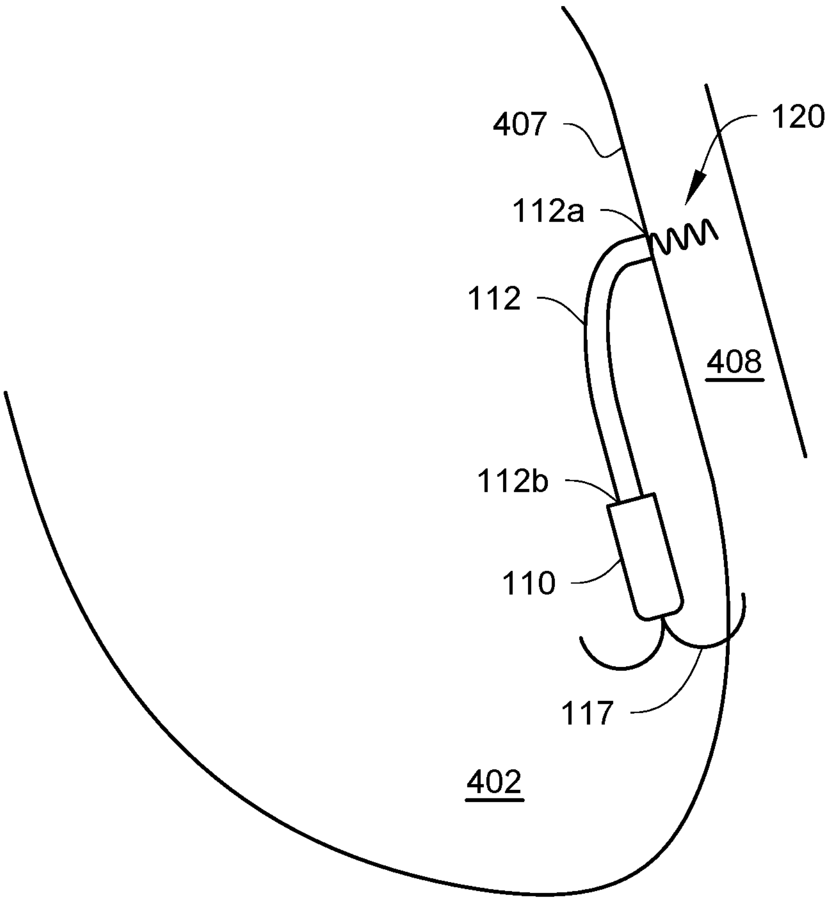
FIG. 7 is a side perspective view of a leadless device implanted in a cardiac conduction system, according to another embodiment.

In various cases, an implantable housing described herein may include a flexible mounting interface extending from a first end to a second end, and connecting with an electrode system at the first end and with the implantable housing at the second end. In the embodiment depicted in FIG. 7, the leadless device includes an electrode system 120 disposed in the septum 408. The mounting interface 112 includes a flexible segment extending between a first end 112*a* and a second end 112*b* to receive electrical connectors (e.g., wires) connecting the electrode system 120 to electronic circuitries inside the housing 110. The flexible segment may have a length in a range, for example, from at or around 20 mm to at or around 80 mm. The flexible segment may have a diameter in a range, for example, at or around 1 mm to at or around 4 mm. The electrode system 120 is connected to the first end 112*a*. The implantable housing 110 is connected to the second end 112*b* and lays against the side wall 407 of the septum 408. A fixation structure 117 is provided on the cap 114 of the housing 110 to hold the implantable housing 110 implantable housing 110 in position so that the housing 110 may be less likely to move around in the heart chamber. The fixation structure 117 may include, for example, a helix structure, a barb structure, a wing structure, or tines for passive fixation at the RV apex. In some cases, the fixation structure 117 may at least partially insert into the septum 408 to anchor the housing 110 in place. While a helix structure is shown in the depicted embodiment of FIG. 7 for the electrode system 120, it is to be understood that the electrode system 120 may include one or more electrodes, one or more fixation structures, and any combinations thereof.

In various cases, an implantable housing and an electronic system of a leadless device described herein may be integrated as a wireless device having a capsule casing. The capsule casing may include a hermetic enclosure to receive electronic circuitries and wireless components. Electrodes are disposed on the outer surface of the capsule casing and electrically connected to the electronic circuitries inside the capsule casing. The electronic circuitries can include a wireless receiver device for wireless power transfer, which extracts from an electromagnetic field generated by a remote transmitter device. The electronic circuitries can further include a pulse generator powered by a battery and a controller to control the pulse generator to deliver and regulate electrical impulses to the electrode system and/or determine sensing signals from the electrode system.

Figure 8A:
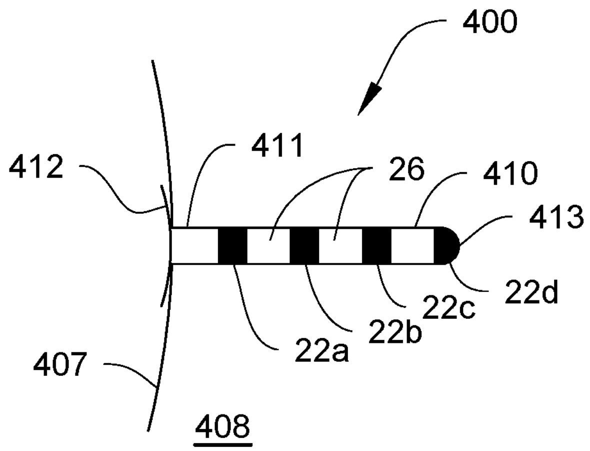
FIG. 8A is a perspective view of a wireless device implanted in a septum, according to an embodiment.

FIG. 8A illustrates a wireless device 400 includes a capsule casing 410 extending from a proximate end 411 to a distal end 413 thereof. The proximate end 411 is connected to a mesh structure 412. The mesh structure 412 is pressed against the side wall 407 of the septum 408 after the capsule casing 410 is inserted into the septum 408. In some cases, the mesh structure 412 may be, for example, a polyester mesh or other mesh structures suitable for surgical and medical device applications. In some cases, the capsule casing 410 can be delivered into the septum 408 via a catheter system including a needle structure. For example, the capsule casing 410 may be connected to a needle structure which can be delivered to the septum via the catheter system such as the catheter system 500 in FIG. 9. When the needle structure is delivered in place, the capsule casing 410 can be released from the catheter system.

Multiple electrodes 22*a*, 22*b*, 22*c*, and 22*d* are disposed as an array on the capsule casing 410 between the proximate end 411 and the distal end 413. In the depicted embodiments, the electrodes 22*a-d* each are a ring electrode disposed around the capsule casing 410 and electrically separated by a spacer 26. The ring electrodes can be made of an electrically conductive material titanium, platinum, platinum-iridium alloy, or the like, and/or coated for increased surface area. The electrodes 22*a-d* are located at different depths of the capsule casing 410 with respect to the proximate end 411, and are electrically connected to the electronic circuitries received by the capsule casing 410. Similar to the varied lengths of the electrodes 12*a-d* in the embodiment of FIG. 2A, the varied depths of the electrodes 22*a-d* in the embodiment of FIG. 8B allow the placing of electrodes at different locations of the septum, and allows for the accommodation of patients' anatomical and/or physiological differences.

The wireless device 400 further includes electronic circuitries received by the capsule casing 410 and electrically connected to the electrodes 22*a-d*. The electronic circuitries may include a wireless communication component, as well as a wireless receiver device for wireless power transfer, a pulse generator, and a controller.

Figure 8B:
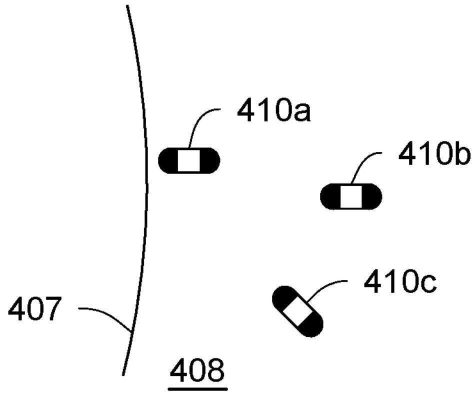
FIG. 8B is a perspective view of a wireless system implanted in a septum, according to an embodiment.

FIG. 8B illustrates a wireless system includes multiple wireless devices 410*a*, 410*b* and 410*c* each including a capsule casing. The wireless devices 410*a*, 410*b* and 410*c* are disposed at different locations of the septum 408 and in wireless communication with each other. While three wireless devices are shown in the embodiment depicted in FIG. 8B, it is to be understood that other numbers (e.g., 2, 4, 5, 6, 7, 8, 9, 10, etc.) of wireless devices can be implanted at various locations of the septum to better target/locate the conduction pathway(s) such as LBB, to reduce (or produce less) heart tissue trauma, to provide a lower and stable pacing threshold, and to provide secured device fixation. In some cases, the wireless devices 410*a*, 410*b* and 410*c* can be respectively delivered into the septum 408 via a catheter system including a needle structure. For example, one wireless device may be connected to a needle structure which can be delivered to the septum via the catheter system such as the catheter system 500 in FIG. 9. When the needle structure is delivered at the desired location, the capsule casing can be released from the catheter system. The catheter system may be reused to deliver another wireless device at a different location in the septum.

Each wireless device may include one or more ring electrodes or other types of electrodes disposed on the respective capsule casings. For each wireless device, the one or more ring electrodes are electrically connected to the electronic circuitries (not shown) received by the respective capsule casings 410*a*, 410*b* and 410*c*. The electronic circuitries may include a wireless communication component, as well as a wireless receiver device for wireless power transfer, a pulse generator, and a controller. Similar to the varied depth of the electrodes 22*a-d* in the embodiment of FIG. 8A, the varied depths/locations of the wireless devices 410*a*, 410*b* and 410*c* in the embodiment of FIG. 8B allow the placing of electrodes at different locations of the septum, and allows for the accommodation of patients' anatomical and/or physiological differences.

Figure 9:
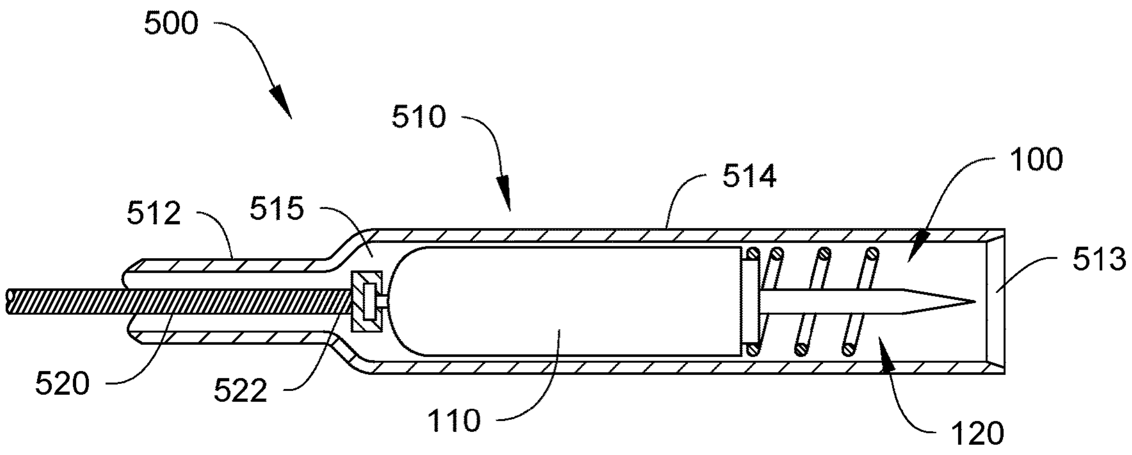
FIG. 9 is a perspective view of a system to implant a leadless device for a cardiac conduction system, according to an embodiment.

FIG. 9 illustrates a catheter system 500 for implanting a leadless device for cardiac conduction system, according to one embodiment. The catheter system 500 provides a delivery catheter 510 including a flexible, deflectable catheter shaft 512 to receive a torque shaft 520. The delivery catheter 510 further includes a catheter housing 514 connecting to the flexible, deflectable catheter shaft 512 at a distal end thereof. The catheter housing 514 has a tubular structure including an orifice 515 (hole, cavity, opening, etc.) to receive a leadless device to be implanted. In some cases, the catheter housing 514 may be at least partially rigid. The orifice 515 has a shape and sizes suitable for accommodating the leadless device. In some cases, an outer diameter of the catheter housing 514 may range, for example, from at or about 10 French to at or about 30 French or more, or at or about 22 French. The delivery catheter 510 can be made of red rubber, latex, silicone, plastic and/or polyvinyl chloride, or the like. In some cases, the catheter housing 514 may have a tubular wall structure that is peelable such that when the leadless device is implanted in place, the tubular wall of the catheter housing 514 can be peeled off to release the leadless device from the delivery catheter 510. In some cases, the catheter system 500 may include an outer guide sheath (not shown) to receive the delivery catheter and guide the delivery.

In the depicted embodiment of FIG. 9, the leadless device 100 of FIG. 1A is illustrated as an exemplary leadless device to be delivered by the catheter system 500. It is to be understood that a leadless device to be implanted can be any leadless devices described herein. The capsule housing 110 of the leadless device 100 may have an outer diameter slightly smaller than the outer diameter of the catheter housing 514. The torque shaft 520 is provided inside the flexible, deflectable catheter shaft 512 to have its distal end 522 rotatablely connecting to the leadless device 100 received by the catheter housing 514. The torque shaft 520 can rotate to drive the electrode system 120 of the leadless device 100 through the opening 513 of the orifice 512 into a heart tissue, e.g., a septum. In some cases, the torque shaft 520 can connect to the leadless device to drive the housing 110 (e.g., connecting to the rotation mechanism 113 of FIG. 1A). In some cases, the torque shaft can connect to at least one of the electrodes to directly drive the electrode (e.g., connecting to the drive screw 162 of FIG. 2). It is to be understood that any suitable drive mechanism can be used to facilitate the rotation of the torque shaft to drive an electrode system of a leadless device into the heart tissue.

Figure 10A:
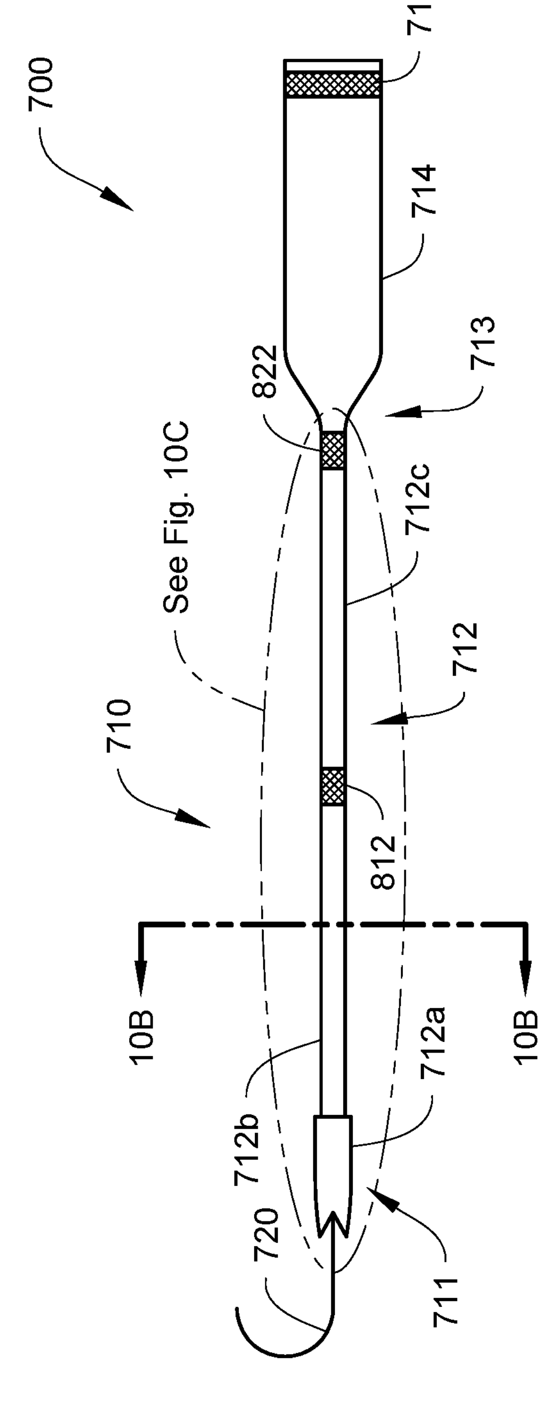
FIG. 10A is a side view of a catheter system to implant a leadless device for a cardiac conduction system, according to another embodiment.

FIG. 10A is a side view of a catheter system 700 to implant a leadless device (not shown) for a cardiac conduction system, according to another embodiment. The catheter system 700 includes a delivery catheter 710 including a flexible, deflectable catheter shaft 712 to receive a torque shaft 720 (such as the torque shaft 520 in FIG. 9). The delivery catheter 710 further includes a catheter housing 714 connecting to the flexible, deflectable catheter shaft 712 at a distal end of the delivery catheter 710. The catheter housing 714 may have similar structure as the catheter housing 514 in FIG. 9, for example, having a tubular structure including an orifice (hole, cavity, opening, etc.) to receive a leadless device/pacemaker to be implanted.

The catheter shaft 712 includes multiple connected sections 712*a*, 712*b* and 712*c* extending between a proximate end 711 and a distal end 713 of the catheter shaft 712. The multiple sections 712*a*, 712*b* and 712*c* may have different stiffness made of, for example, material(s) (e.g., polymeric materials) with different hardness as measured by a Shore durometer (D) hardness test under ASTM D2240 type A. The section 712*c* that connects to the catheter housing 714 at the distal end 713 may have less stiffness compared to other sections. As an example, the sections 712*a*, 712*b*, 712*c* and the catheter housing 714 may have Shore durometer (D) hardness values under ASTM D2240 type A of at or around 67 to at or around 77, at or around 57 to at or around 67, at or around 50 to at or around 60, and at or around 67 to at or around 77, respectively. It is to be understood that the catheter shaft 712 may include more than three multi-sections constructed with material(s) with different/suitable durometers. As an example, the sections 712*b* and 712*c* connected to the catheter housing 714, and the catheter housing 714 may have lengths of at or around 35 mm, at or around 25 mm and at or around 40 mm, respectively. As an example, the catheter housing 714 may have an inner diameter at or about 7 mm at the distal tip as indicated by a tip marker 71. The tip marker 71 can be a plastic loaded with radiopaque filler (e.g., tungsten carbide, bismuth sub carbonate, barium sulfide) or have a platinum marker band. It is to be understood that the multiple sections 712*a*, 712*b* and 712*c*, and the catheter housing 714 may have other suitable values for stiffness, lengths, diameters, and other dimensions. While three sections 712*a*, 712*b*, 712*c* are illustrated in the embodiment of FIG. 10A, it is to be understood that multiple sections (e.g., 2 sections, 4 sections, or more sections) with the respective stiffness values can be provided to obtain the desired flexibility and deflection.

Figure 10B:
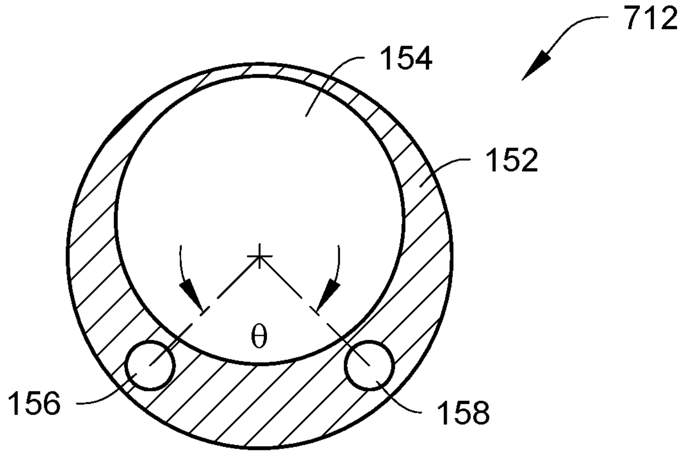
FIG. 10B is a cross-sectional view of a delivery catheter of FIG. 10A.
Figure 10C:
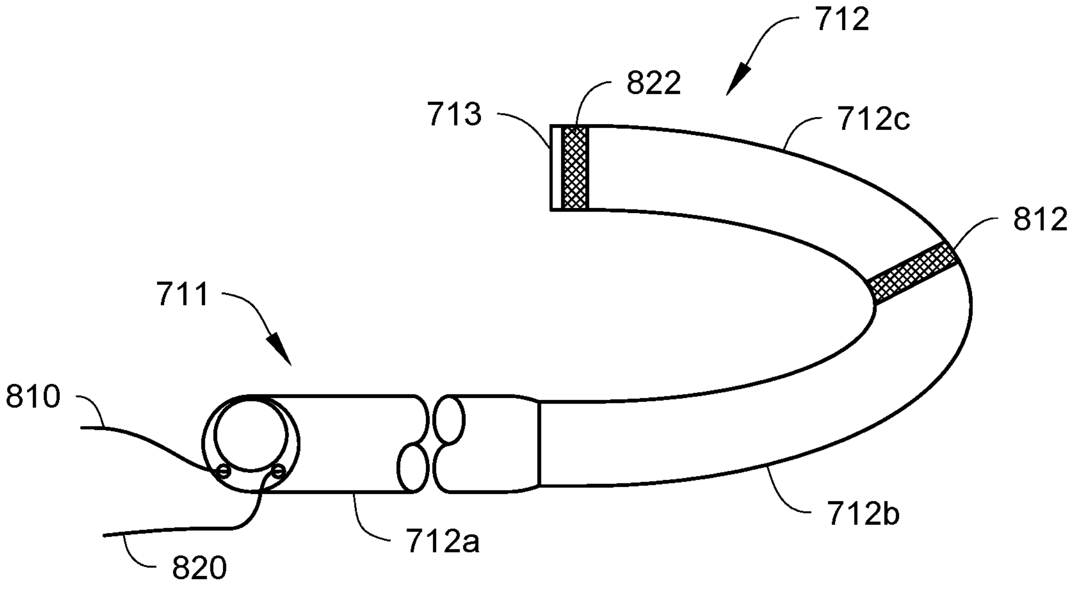
FIG. 10C is a perspective view of a portion of a delivery catheter of FIG. 10A.

FIG. 10B is a cross-sectional view of the catheter shaft 712 of FIG. 10A. FIG. 10C is a perspective view of a portion of the catheter shaft 712 of FIG. 10A. In the cross-sectional view (e.g., cut by a plane perpendicular to a length direction of the catheter shaft), the catheter shaft 172 includes a body (tube) 152 and an orifice (hole, cavity, opening, etc.) 154 extending from the proximal end 711 of the catheter shaft 712 to the distal end 713 connecting to the catheter housing 714 for implanting a leadless device. The orifice 154 has a size suitable to receive a torque shaft such as the torque shaft 520 in FIG. 9. The torque shaft extends in the orifice 154 and has its distal end connected to a leadless device received in the catheter housing 714. In an embodiment, a diameter of the orifice 154 ranges, for example, from at or about two French to at or about ten French or more. In an embodiment, the catheter shaft 712 may include a Polytetrafluoroethylene (PTFE) inner liner, a stainless steel braid, and a Polyether block amide (PEBA) or polyurethane outer jacket.

In an embodiment, the catheter shaft 712 can include a first opening (hole, cavity, orifice, etc.) 156 and a second opening 158. The first opening 156 is configured to accommodate a first deflection wire 810, and the second opening 158 is configured to accommodate a second deflection wire 820. The first opening 156 and the first deflection wire 810 therein extend from the proximate end 711 of the catheter shaft 712 to a distal end of the section 712*b*, where the first deflection wire 810 connects to a first ring structure 812 mounted on the catheter shaft 712. The second opening 158 and the second deflection wire 820 therein extend from the proximate end 711 of the catheter shaft 712 to a distal end of the section 712*c*, where the second deflection wire 820 connects to a second ring structure 822 mounted on the catheter shaft 712. The first ring structure 812 is located at the junction connecting the sections 712*b* and 712*c*. The second ring structure 822 is located at the junction connecting the section 712*c* and the catheter housing 714. The first deflection wire 810 and the second deflection wire 820 are configured to be pulled (e.g., by a user such as a physician) to deflect the catheter shaft 712 at different locations of the delivery catheter 710. In the depicted embodiment, the ring structure is a weld ring to hold the distal end of a deflection wire in place. It is to be understood that any suitable fixation structures can be used to hold the distal end of a deflection wire in place. While two deflection wires and the corresponding ring structures are illustrated in the embodiment of FIGS. 10A-C, it is to be understood that one or more deflection wires (e.g., one deflection wire, 3 deflection wires, 4 deflection wires, 5 or more deflection wires) with the corresponding ring structures can be provided to obtain the desired deflection at different locations.

In an embodiment, the catheter shaft 712 can be of bi-directional deflection on the same plane or on different planes. For example, the first deflection wire 810 is configured to be pulled to deflect the distal end of the section 712*b* of the catheter shaft 712 in a first plane (e.g., an X-Y plane in an X-Y-Z Cartesian coordinate system). The second deflection wire 820 is configured to be pulled to deflect the distal end of the section 712*c* of the catheter shaft 712 in the same X-Y plane, or in a second plane (e.g., a Z-Y plane or a Z-X plane in the X-Y-Z Cartesian coordinate system) perpendicular to the first plane. It is to be understood that the second plane may or may not be perpendicular to the catheter deflection on the first plane. The first deflection wire 810 and the second deflection wire 820 are spaced apart at a central angle (θ) from a center of the catheter in a cross-sectional view (see FIG. 10B). In an embodiment, the angle θ can be, for example, at or around 90 degrees to at or around 180 degrees to achieve the desired deflection. As an example, when the angle θ is at or around 180 degrees, the first deflection wire 810 can be pulled to deflect the section 712*b* upward, and the second deflection wire 810 can be pulled to deflect the section 712*c* downward.

It will be appreciated that the first deflection wire 810 and the second deflection wire 820 connect to the respective locations of the catheter shaft 712 so that the respective locations of the catheter shaft 712 can be deflected when the corresponding deflection wire is pulled. It will also be appreciated that positioning catheter housing 714 against a septum can include one or more of the steps of pulling the first deflection wire 810 to deflect the distal end of the section 712*b* (e.g., pulling the first deflection wire 810 to deflect the distal end of the section 712*b* in a first plane), pulling the second deflection wire 820 to deflect the distal end of the section 712*c* (e.g., pulling the second deflection wire 820 to deflect the distal end of the section 712*c* in a second plane perpendicular to the first plane, or pulling the second deflection wire 820 to deflect the distal end of the catheter housing 714), and positioning the distal end of the catheter housing 714 to be perpendicular to an endocardial surface of the septum.

Figure 11A:
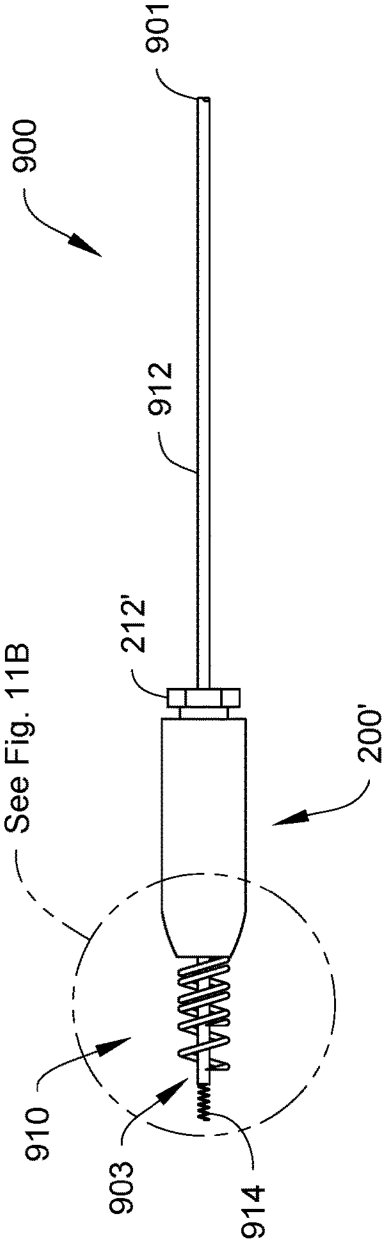
FIG. 11A is a side perspective view of a delivery system including a guidewire to implant a leadless device for a cardiac conduction system, according to an embodiment.
Figure 11B:
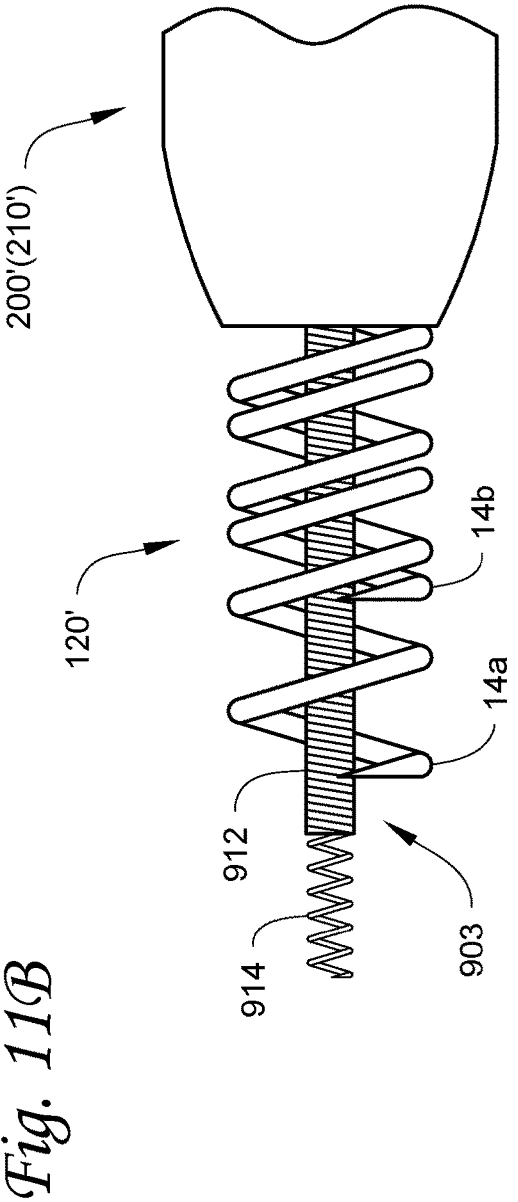
FIG. 11B is an enlarged perspective view of a portion of the delivery system of FIG. 11A.

FIG. 11A is a side perspective view of a delivery system 900, engaged with a leadless CSP pacemaker, including a guidewire 910 which has a proximal end 901 and a distal end 903 affixed with a helix, to implant a leadless device/pacemaker 200' for a cardiac conduction system, according to an embodiment. FIG. 11B is an enlarged perspective view of a portion of the system 900 of FIG. 11A. The leadless device 200' includes a leadless pacemaker or an implantable housing 210' similar to the implantable housing 210 in FIG. 2. The implantable housing 210' has a tubular structure with a through hole extending along its longitudinal direction. The housing 210' may have a length, for example, at or around 10 mm to at or around 40 mm, or at or around 20 mm to at or around 30 mm, and may have an outer diameter, for example, at or around 5 mm to at or around 10 mm. The electrode system 120' of the leadless device 200' includes a first helix electrode 14*a* and a second helix electrode 14*b* which are co-axial. The first helix electrode 14*a* has a distal end which is distal to a distal end of the second helix electrode 14*b*. The electrodes 14*a* and 14*b* are electrically connected to electronic circuitries received in a hermetic enclosure of the tubular structure of the implantable housing 210'. In some cases, the helix electrodes 14*a*, 14*b* each alone or in combination can be a bipolar electrode. It is to be understood that the electrode system 120' may include any electrodes described herein and/or their combinations.

The guidewire 910 includes a wire 912 extending from a proximate end 901 to a distal end 903. A helix tip 914 is disposed at the distal end 903 of the wire 912. The wire 912 extends through the through hole of the leadless pacemaker (or an implantable housing) 210', and extends through the inner space defined by the first helix electrode 14*a* and the second helix electrode 14*b* such that the helix tip 914 projects from the distal end of the leadless device 200'. In some cases, the wire 912 may be a conductive wire covered by a non-conductive insulation layer and can be radiopaque to facilitate implanting and/or locating the wire. The proximal end 901 of the wire 912 can be exposed from the insulation layer. The proximal end 901 can be integrated into a connector (not shown) configured to connect to e.g., a signal processing device (having a controller) for mapping the conduction system. The helix tip 914 may have an outer diameter, for example, at or around 0.3 mm to at or around 0.8 mm, or at or around 0.5 mm. The helix tip 914 may have a length, for example, at or around 1 mm to at or around 10 mm. The helix tip 914 may be made of any materials suitable for a fixation structure discussed above. The wire 912 may have a diameter, for example, at or around 0.5 mm to at or around 2 mm, or at or around at or around 0.9 mm. The wire 912 extends through the capsule housing 210' via its through hole which may have a diameter slightly greater than the diameter of the wire 912.

The helix tip 914 may act as a fixation mechanism for over-the-wire delivery during the implantation procedure, a mapping electrode, or both. In some cases, the helix tip 914 at the distal end 903 of the wire 912 can be configured to identify and/or locate a target or desired location (e.g., His bundle, RBB, LBB, etc.) of the cardiac conduction system prior to implanting the leadless device 200'. Identifying the target location (e.g., His bundle, RBB, LBB, etc.) of the cardiac conduction system can be referred to as "mapping" or "electrically mapping" of the cardiac conduction system. For example, the helix tip 914 can be placed on/against the surface of the septum or be inserted to the ventricular septum to locate a cardiac conduction system pathway such as the RBB or the LBB. The proximal end 901 of the wire 912 can be configured to connect to a device (implantable or external, not shown in the figures) that can be used to control the guidewire 910.

Figure 12A:
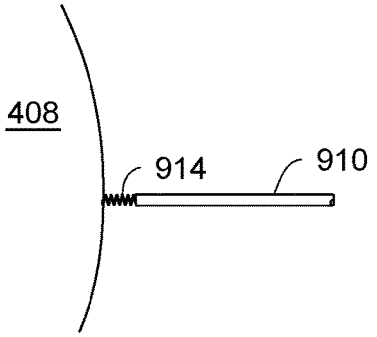
FIGS. 12A-12E are schematic diagrams illustrating a leadless device for a cardiac conduction system being implanted, according to an embodiment.
Figure 12B:
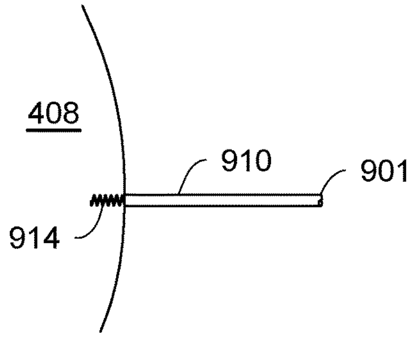

FIGS. 12A-12E are schematic diagrams illustrating a leadless device being implanted using the delivery system 900 of FIG. 11A, according to an embodiment. As shown in FIG. 12A, the guidewire 910 is delivered to an implant site (e.g., the septum 408) via an appropriate delivery catheter (not shown in the figures). A suitable delivery catheter may include a flexible, deflectable catheter shaft such as, for example, the catheter shaft 712 in FIG. 10A. The helix tip 914 of the guidewire 910 can be screwed into the septum 408 and fixated therein by, for example, rotating the guidewire 910 at its proximate end 901. As shown in FIG. 12B, the helix tip 914 of the guidewire 910 can be positioned into the septum (e.g., by screwing into the septum). The device (not shown) connected to the proximate end 901 of the wire 912 can deliver electrical impulses (e.g., a burst of energy) through the wire 912 (from the proximal end 901 to the distal end 903) to the septum (e.g., at or around pathway (s) of the cardiac conduction system) of the cardiac conduction system, to stimulate the myocardium and/or the cardiac conduction system. Sensing can be conducted to detect the electrocardiogram of the heart or the electrical potential of the cardiac conduction system during the stimulation (e.g., response of the heart evoked by the pacing) to identify the target location (e.g., His bundle, RBB, LBB, etc.) of the cardiac conduction system, which can be referred to as "mapping" or "electrically mapping" of the cardiac conduction system. In some cases, an algorithm can be executed to determine whether the detected electrocardiogram of the stimulation during or after the pacing is a desired electrocardiogram. If yes, the location of the helix tip 914 of the guidewire is determined to be the desired location. If not, the helix tip 914 of the guidewire needs to be moved/adjusted, and the pacing and sensing sequence is to be conducted again to determine the desired location. After the guidewire 910 has its distal end 903 fixed to the septum 408, the delivery catheter is removed from the body (not shown in the figures).

Figure 12C:
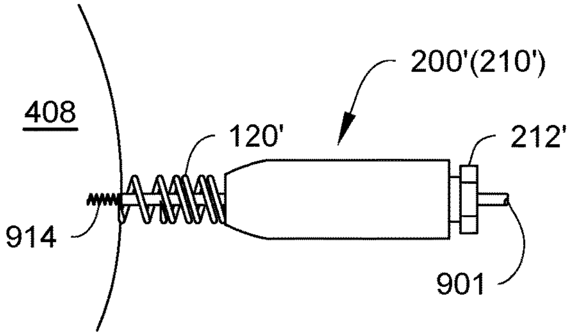
Figure 12D:
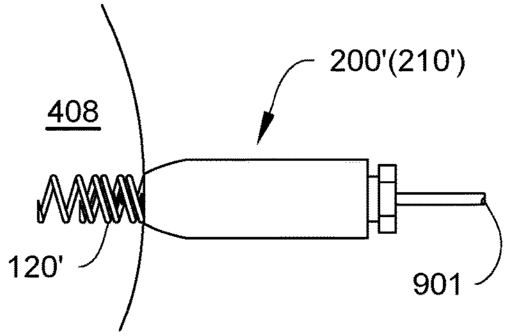
Figure 12E:
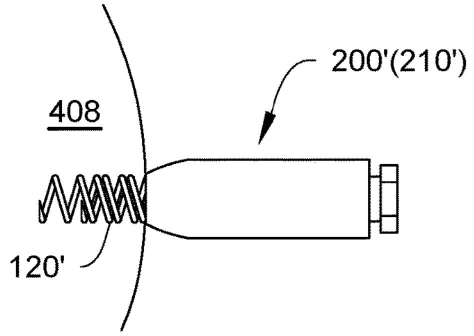

When the desired location is determined (and marked by the helix tip 914 of the guidewire 910), the leadless device 200' can be delivered over the guidewire 910 such that the guidewire 910 extends through a through hole of the housing 210'. As shown in FIG. 12C, when the guidewire 910 is in place with the helix tip 914 being fixated in the septum 408, the leadless device 200' is delivered over the guidewire 910 using a capsule delivery or torque tool (not shown). A suitable capsule delivery or torque tool may have a structure similar to the torque shaft 520 in FIG. 9, which can be connected to a rotation mechanism 212' at the proximate end of the implantable housing 210' to push the implantable housing 210' over the guidewire 910 and screw the helix electrodes 120' into the septum 408. As shown in FIG. 12D, the leadless device 200' is fixated at the implant site (e.g., the septum 408) by applying a rotation torque such that the electrode system 120' (e.g., the helix electrodes 14*a*, 14*b*) are inserted into the septum 408. As shown in FIG. 12E, when the leadless device 200' is in place, the helix tip 914 of the guidewire 910 can be removed from the septum 408 along with the wire 912 by applying a rotation torque. The capsule delivery system can then be disengaged and withdrawn from the body.

Aspects:

It is appreciated that any one of aspects can be combined with other aspect(s).

Aspect 1 is a leadless pacemaker for a cardiac conduction system, comprising:

an implantable housing including a mounting interface;

an electronic circuitry and a power source received by the implantable housing; and an electrode system connected to the electronic circuitry via the mounting interface, the electrode system comprising one or more electrodes configured to insert into a ventricular septum and having a length to reach one or more of pathways of the cardiac conduction system.

Aspect 2 is the pacemaker according to aspect 1, wherein the one or more electrodes includes a plurality of electrodes located at different distances with respect to the mounting interface.

Aspect 3 is the pacemaker according to aspect 1 or 2, wherein the one or more electrodes includes a plurality of linear electrodes each extending from the mounting interface to a tapered tip thereof, the plurality of linear electrodes having different lengths measured between the mounting interface and the respective tapered tips.

Aspect 4 is the pacemaker according to any one of aspects 1-3, wherein the electrode system further comprises a rod extending from the mounting interface to a distal end thereof, and the one or more electrodes are disposed as an array on the rod between the mounting interface and the distal end.

Aspect 5 is the pacemaker according to aspect 4, wherein the electrode system further comprises a helix structure at the distal end of the rod.

Aspect 6 is the pacemaker according to aspect 4 or 5, wherein the electrode system further comprises a barb structure at the distal end of the rod.

30 Aspect 7 is the pacemaker according to any one of aspects 1-6, wherein the electrode system further comprises a helical ribbon structure extending from the mounting interface to a distal end thereof, and the one or more electrodes are disposed on the helical ribbon structure between the mounting interface and the distal end.

Aspect 8 is the pacemaker according to any one of aspects 1-7, wherein the one or more electrodes includes a linear electrode extending from the mounting interface to a tapered tip thereof, and a first helix structure coaxial with the linear electrode and extending from the mounting interface, the first helix structure having an inner diameter greater than an outer diameter of the linear electrode.

Aspect 9 is the pacemaker according to aspect 8, wherein the electrode system further comprises a second helix structure coaxial with the first helix structure and extending from the mounting interface to a tip thereof, the tip of the first helix structure being distal to the tip of the second helix structure.

Aspect 10 is the pacemaker according to any one of aspects 1-9, wherein the electrode system further comprises a first helix structure and a second helix structural coaxially extending from the mounting interface to a tip thereof, the tip of the first helix structure being distal to the tip of the second helix structure.

Aspect 11 is the pacemaker according to aspect 10, wherein the first and second helix structures have substantially the same diameters.

Aspect 12 is the pacemaker according to aspect 10, wherein the second helix structure has an outer diameter greater than an outer diameter of the first helix structure.

Aspect 13 is the pacemaker according to any one of aspects 10-12, wherein the electrode system further comprises a linear electrode extending from the mounting interface to a tapered tip thereof, the first and second helix structures wrapping around the linear electrode and each having an inner diameter greater than an outer diameter of the linear electrode.

Aspect 14 is the pacemaker according to any one of aspects 1-13, wherein the mounting interface includes a mesh structure.

Aspect 15 is the pacemaker according to any one of aspects 1-14, wherein the mounting interface further includes a flexible segment having a first end connecting to the electrode system, and a second end connecting to the implantable housing.

Aspect 16 is the pacemaker according to any one of aspects 1-15, wherein the implantable housing includes a first segment including the mounting interface, a second segment, and a flexible segment connecting the first segment and the second segment.

Aspect 17 is the pacemaker according to aspect 16, wherein the first segment receives the electronic circuitry, and the second segment receives the power source.

Aspect 18 is the pacemaker according to any one of aspects 1-17, wherein the implantable housing further includes a fixation mechanism at an end thereof opposite the mounting interface.

Aspect 19 is the pacemaker according to any one of aspects 1-18, wherein the implantable housing further includes a rotation mechanism at an end thereof opposite the mounting interface.

Aspect 20 is the pacemaker according to any one of aspects 1-19, wherein the electrode system further includes a catheter to receive a helix structure in a straightened state, and the catheter having a distal opening to allow the helix structure to be deployed out of the catheter to restore a helix profile.

Aspect 21 is the pacemaker according to any one of aspects 1-20, wherein the mounting interface further includes a bendable portion such that the implantable housing forms an angle with respect to the electrode system in a range from at or around 60 degrees to at or around 120 degrees.

Aspect 22 is the pacemaker according to any one of aspects 1-21, wherein the power source further includes one or more batteries.

Aspect 23 is the pacemaker according to any one of aspects 1-22, wherein the power source further includes one or more wireless power components.

Aspect 24 is the pacemaker according to any one of aspects 1-23, wherein the electronic circuitry further includes a pulse generator.

Aspect 25 is the pacemaker according to any one of aspects 1-24, wherein the implantable housing has a tubular structure including a cavity to receive the electrode system.

Aspect 26 is the pacemaker according to aspect 25, wherein the tubular structure includes a hermetic enclosure to receive the electronic circuitry.

Aspect 27 is the pacemaker according to aspect 25 or 26, wherein the implantable housing further includes a driving mechanism to drive the electrode system at least partially out of the cavity.

Aspect 28 is the pacemaker according to any one of aspects 1-27, wherein the implantable housing has a tubular structure including a through hole to receive a guidewire.

Aspect 29 is a wireless pacemaker for a cardiac conduction system, comprising:

an implantable housing;

an electronic circuitry and a battery or a wireless power source received by the capsule casing; and an electrode system disposed on an outer surface of the capsule casing and connected to the electronic circuitry inside the capsule casing.

Aspect 30 is the wireless pacemaker according to aspect 29, wherein the electrode system comprises an array of electrodes disposed on the outer surface of the capsule casing.

Aspect 31 is the wireless pacemaker according to aspect 29 or 30, further comprising a mesh structure connected to the capsule casing at a proximate end thereof.

Aspect 32 is the wireless pacemaker according to any one of aspects 29-31, wherein the implantable housing comprises a plurality of capsule casings each configured to receive an electronic circuitry powered by a wireless power source and in wireless communication with each other.

Aspect 33 is a delivery system to deliver the pacemaker according to any one of aspects 1-32, the delivery system comprising:

a torque shaft; and a delivery catheter including a flexible, deflectable catheter shaft to receive the torque shaft, and a catheter housing connecting to the flexible, deflectable catheter shaft at a distal end of the delivery catheter, the catheter housing being configured to receive the pacemaker, and the torque shaft extending in the flexible, deflectable catheter shaft and having a distal end rotatablely connected to the pacemaker.

Aspect 34 is the system according to aspect 33, wherein the torque shaft connects to the implantable housing of the pacemaker.

Aspect 35 is the system according to aspect 33 or 34, wherein the torque shaft connects to at least one of the one or more electrodes.

Aspect 36 is the system according to any one of aspects 33-35, wherein the catheter shaft includes a plurality of sections connected to each other, the plurality of sections having different values of stiffness and including one or more materials with different hardness measured under ASTM D2240 type A.

Aspect 37 is the system according to aspect 36, further including one or more deflection wires, and wherein the catheter shaft further includes one or more openings configured to accommodate the one or more deflection wires.

Aspect 38 is the system according to aspect 37, wherein the one or more deflection wires are configured to be pulled to deflect one or more of the plurality of sections of the catheter shaft.

Aspect 39 is the system according to aspect 37 or 38, wherein the catheter shaft further includes one or more ring structures disposed at connections between the adjacent sections of the catheter shaft, and the one or more deflection wires are connected to the one or more ring structures, respectively.

Aspect 40 is a delivery system to deliver the pacemaker according to any one of aspects 1-32, the system comprising:

a guidewire including a wire configured to extend through a through hole of the pacemaker; and a helix tip disposed at a distal end of the wire and configured to be a fixation mechanism and/or a mapping electrode.

Aspect 41 is a method of implanting a leadless pacemaker for a cardiac conduction system, the method comprising:

positioning the leadless pacemaker inside a catheter;

inserting the catheter to reach a septum;

positioning the catheter against the septum;

engaging at least one electrode of the leadless pacemaker to the septum; and removing the catheter.

Aspect 42 is the method according to aspect 41, wherein engaging the at least one electrode of the leadless pacemaker to the septum further includes rotating a torque shaft having an end connected to the leadless pacemaker.

Aspect 43 is a method of implanting a leadless pacemaker for a cardiac conduction system, the method comprising:

delivering a guidewire to reach a septum, wherein the guidewire includes a wire and helix tip disposed at a distal end of the wire;

fixating the helix tip of the guidewire into the septum;

positioning a leadless pacemaker such that the guidewire extends through a through hole of the leadless pacemaker;

delivering the leadless pacemaker over the guidewire to reach the septum;

engaging at least one electrode of the leadless pacemaker to the septum; and removing the guidewire from the septum.

The terminology used in this specification is intended to describe particular embodiments and is not intended to be limiting. The terms "a," "an," and "the" include the plural forms as well, unless clearly indicated otherwise. The terms "comprises" and/or "comprising," when used in this specification, specify the presence of the stated features, integers, steps, operations, elements, and/or components, but do not preclude the presence or addition of one or more other features, integers, steps, operations, elements, and/or components.

With regard to the preceding description, it is to be understood that changes may be made in detail, especially in matters of the construction materials employed and the shape, size, and arrangement of parts without departing from the scope of the present disclosure. This specification and the embodiments described are exemplary only, with the true scope and spirit of the disclosure being indicated by the claims that follow.

What is claimed is:

1. A leadless pacemaker for a cardiac conduction system, comprising:

an implantable housing including a mounting interface;

an electronic circuitry and a power source received by the implantable housing; and an electrode system connected to the electronic circuitry via the mounting interface, the electrode system comprising a first electrode and a first helix structure independent of each other, configured to be inserted into a septum, and each having a length to penetrate one or more of pathways of the cardiac conduction system, wherein the first electrode and the first helix structure are configured to be independently advanceable relative to each other in an axial direction.

2. The pacemaker according to claim 1, wherein the first electrode is a linear electrode extending from the mounting interface to a tapered tip thereof, the first helix structure is coaxial with the linear electrode and extends from the mounting interface, and the first helix structure has an inner diameter greater than an outer diameter of the linear electrode.

3. The pacemaker according to claim 1, wherein the first electrode is a second helix structural, the first helix structure and the second helix structural coaxially extend from the mounting interface to a tip thereof, the tip of the first helix structure is distal to the tip of the second helix structure.

4. The pacemaker according to claim 1, wherein the mounting interface includes a mesh structure.

5. The pacemaker according to claim 1, wherein the mounting interface further includes a flexible segment having a first end connecting to the electrode system, and a second end connecting to the implantable housing.

6. The pacemaker according to claim 1, wherein the implantable housing includes a first segment including the mounting interface, a second segment, and a flexible segment connecting the first segment and the second segment.

7. The pacemaker according to claim 1, wherein the implantable housing further includes a fixation mechanism at an end of the implantable housing opposite the mounting interface.

8. The pacemaker according to claim 1, wherein the implantable housing further includes a rotation mechanism at an end of the implantable housing opposite the mounting interface.

9. The pacemaker according to claim 1, wherein the electrode system further includes a catheter to receive a helix structure in a straightened state, and the catheter having a distal opening to allow the helix structure to be deployed out of the catheter to restore a helix profile.

10. The pacemaker according to claim 1, wherein the mounting interface further includes a bendable portion such that the implantable housing forms an angle with respect to the electrode system in a range from at or around 60 degrees to at or around 120 degrees.

11. The pacemaker according to claim 1, wherein the implantable housing has a tubular structure including a through hole to receive a guidewire.

12. A delivery system to deliver the pacemaker according to claim 1, the system comprising:

a torque shaft; and a delivery catheter including a flexible, deflectable catheter shaft to receive the torque shaft, and a catheter housing connecting to the flexible, deflectable catheter shaft at a distal end of the delivery catheter, the catheter housing being configured to receive the pacemaker, and the torque shaft extending in the flexible, deflectable catheter shaft and having a distal end rotatablely connected to the pacemaker.

13. The system according to claim 12, wherein the catheter shaft includes a plurality of sections connected to each other, the plurality of sections having different values of stiffness and including one or more materials with different hardness measured under ASTM D2240 type A.

14. The system according to claim 13, further including one or more deflection wires configured to be pulled to deflect one or more of the plurality of sections of the catheter shaft.

15. A delivery system to deliver the pacemaker according to claim 1, the system comprising:

a guidewire including a wire configured to extend through a through hole of the pacemaker; and a helix tip disposed at a distal end of the wire and configured to be a fixation mechanism or a mapping electrode.

16. The pacemaker according to claim 1, wherein the first electrode is configured to move proximally with respect to the first helix structure such that a distal end of the first electrode is proximal to a distal end of the first helix structure in a retracted state, and the first electrode is configured to move distally with respect to the first helix structure such that the distal end of the first electrode is distal to the distal end of the first helix structure in an extended state.

17. The pacemaker according to claim 1, wherein the first helix structure is configured to move distally with respect to the first electrode such that a distal end of the first electrode is proximal to a distal end of the first helix structure in a retracted state, and the first helix structure is configured to move proximally with respect to the first electrode such that the distal end of the first electrode is distal to the distal end of the first helix structure in an extended state.

18. The pacemaker according to claim 1, wherein the first electrode is a linear electrode having a length of at or around 12 mm, the linear electrode includes a distal electrode section having a length of at or around 4 mm and a non-conductive section, and the first helix structure has a length of at or around 4 mm.

19. The pacemaker according to claim 18, wherein the linear electrode further includes a proximal electrode section having a length of at or around 4 mm, and the non-conductive section has a length of at or around 4 mm.

20. The pacemaker according to claim 1, wherein the implantable housing has an outer diameter in a range from at or around 1 mm to at or around 10 mm.

* * * * *